United States Patent
Moreaux et al.

(10) Patent No.: US 10,676,791 B2
(45) Date of Patent: Jun. 9, 2020

(54) METHODS FOR PREDICTING RESPONSE TO DNA REPAIR PATHWAY INHIBITORS IN DIFFUSE LARGE B-CELL LYMPHOMA

(71) Applicants: INSERM (INSTITUT NATIONAL DE LA SANTÉ ET DE LA RECHERCHE MÉDICALE), Paris (FR); UNIVERSITE DE MONTPELLIER, Montpellier (FR); CENTRE HOSPITALIER UNIVERSITAIRE DE MONTPELLIER, Montpellier (FR); CENTRE NATIONAL DE LA RECHERCHE SCIENTIFIQUE (CNRS), Paris (FR)

(72) Inventors: Jerome Moreaux, Montpellier (FR); Guillaume Cartron, Montpellier (FR); Caroline Bret, Montpellier (FR); Angelos Constantinou, Montpellier (FR); Philippe Pasero, Montpellier (FR)

(73) Assignees: INSERM(INSTITUT NATIONAL DE LA SANTE ET DE LA RECHERCHE MEDICALE), Paris (FR); UNIVERSITE DE MONTPELLIER, Montpellier (FR); CENTRE HOSPITALIER UNIVERSITAIRE DE MONTPELLIER, Montpellier (FR); CENTRE NATIONAL DE LA RECHERCHE SCIENTIFIQUE (CNRS), Paris (FR)

(*) Notice: Subject to any disclaimer, the term of this patent is extended or adjusted under 35 U.S.C. 154(b) by 649 days.

(21) Appl. No.: 15/328,918

(22) PCT Filed: Jul. 27, 2015

(86) PCT No.: PCT/EP2015/067174
§ 371 (c)(1),
(2) Date: Jan. 25, 2017

(87) PCT Pub. No.: WO2016/012630
PCT Pub. Date: Jan. 28, 2016

(65) Prior Publication Data
US 2017/0211151 A1  Jul. 27, 2017

(30) Foreign Application Priority Data

Jul. 25, 2014 (EP) .................... 14306201

(51) Int. Cl.
*G01N 33/48* (2006.01)
*C12Q 1/6886* (2018.01)
(Continued)

(52) U.S. Cl.
CPC .......... *C12Q 1/6886* (2013.01); *G16B 20/00* (2019.02); *G16H 50/30* (2018.01);
(Continued)

(58) Field of Classification Search
None
See application file for complete search history.

(56) References Cited

U.S. PATENT DOCUMENTS

| 7,858,331 B2 | 12/2010 | D'Andrea et al. |
| 2009/0062196 A1 | 3/2009 | D'Andrea et al. |

(Continued)

FOREIGN PATENT DOCUMENTS

| WO | 2006/135763 A2 | 12/2006 |
| WO | 2008/066624 A2 | 6/2008 |
| WO | 2014/056928 A1 | 4/2014 |

OTHER PUBLICATIONS

Hoheisel, "Microarray technology: beyond transcript profiling and genotype analysis", Nature Reviews Genetics, 2006, pp. 200-210, vol. 7.

(Continued)

*Primary Examiner* — Anna Skibinsky
(74) *Attorney, Agent, or Firm* — Young & Thompson

(57) ABSTRACT

The present invention relates to a method of testing whether a patient suffering from arge B-cell lymphoma will respond or not to a DNA repair pathway inhibitor comprising: i) determining the expression level (ELi) of several genes Gi-Gn selected from table A in a biological sample obtained from said patient comparing the expression level (ELi) determined at step i) with a predetermined reference level (ELRi) iii) calculating the DNA repair score trough the following formula (I), wherein βi represent the regression β coefficient reference value for the gene Gi and Ci=1 if the expression of the gene Gi (ELi) is higher than the predetermined reference level (ELRi) or Ci=−1 if the expression of the gene (ELi) is lower than or equal to the predetermined reference level (ELRi) iv) comparing the score DNARS determined at step iii) with a predetermined reference value $DNARS_R$ v) and concluding that the patient will respond to the treatment when the DNARS score is higher than the predetermined reference value $DNARS_g$ or concluding that the patient will not respond to the treatment when the DNARS score is lower than the predetermined reference value $DNARS_R$.

Figure 1A:
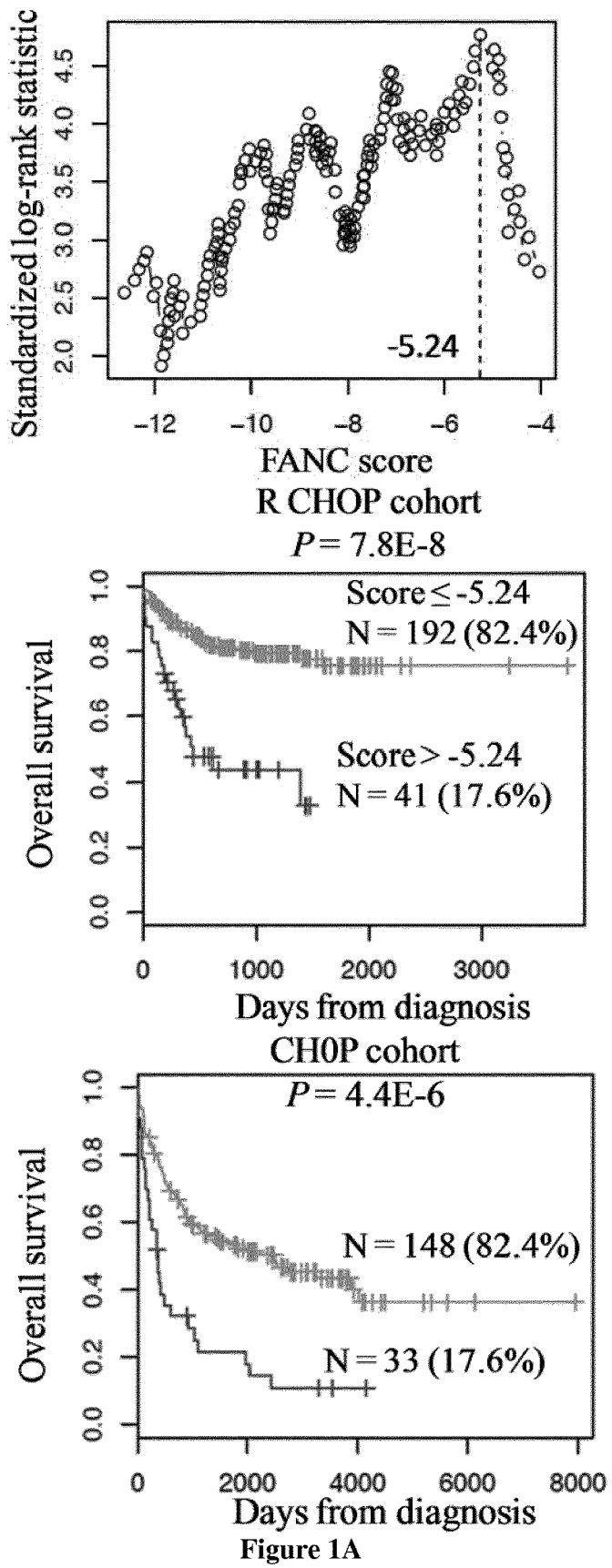
Figure 1B:
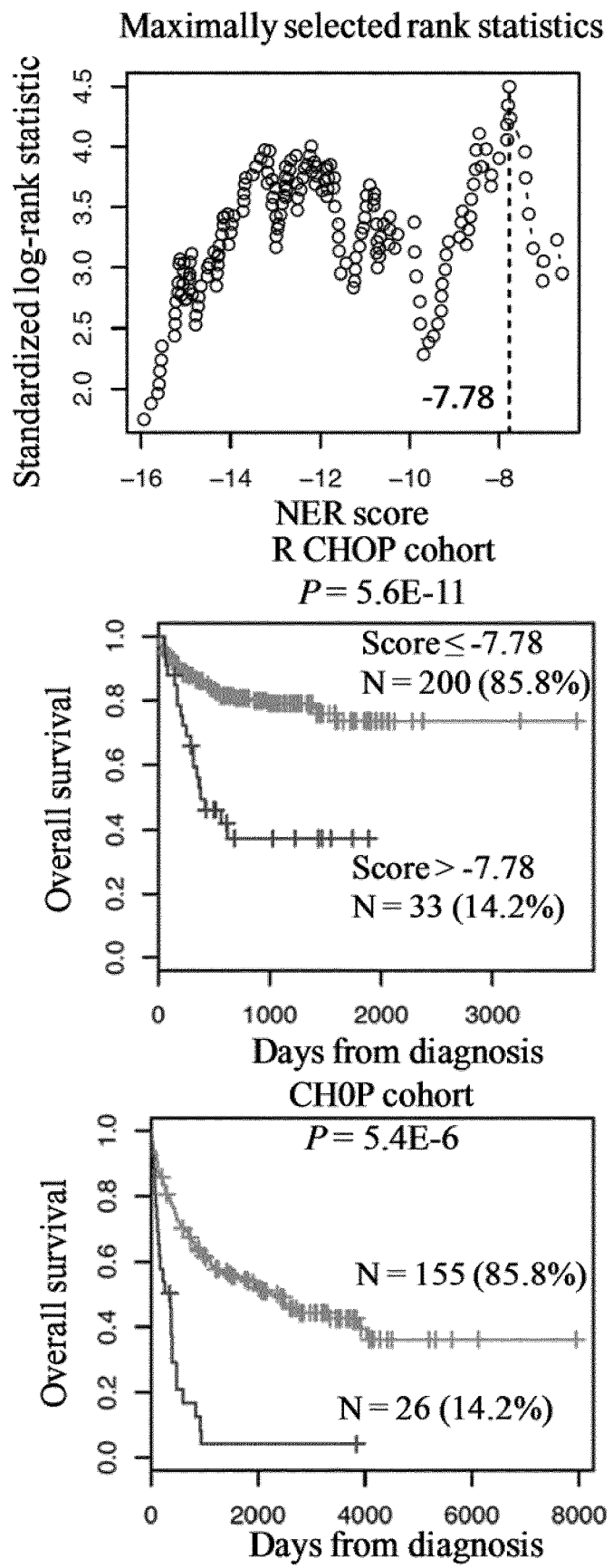
Figure 1C:
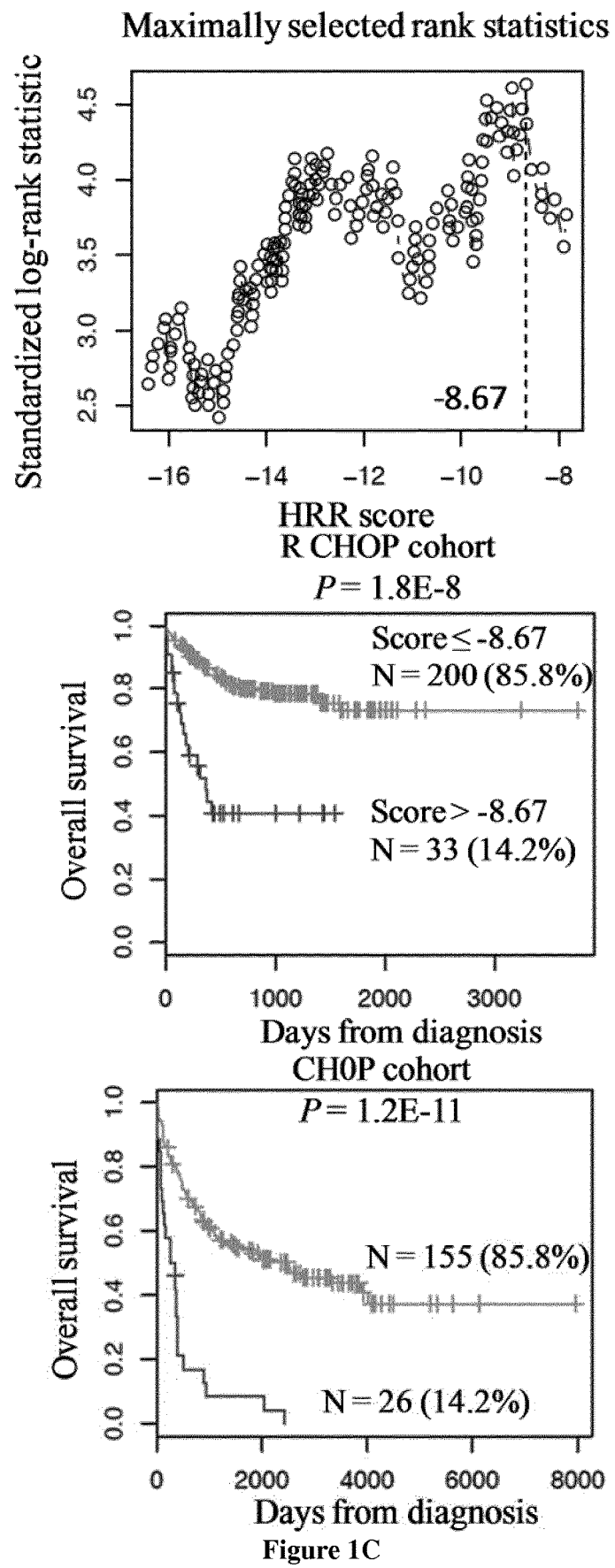
Figure 1D:
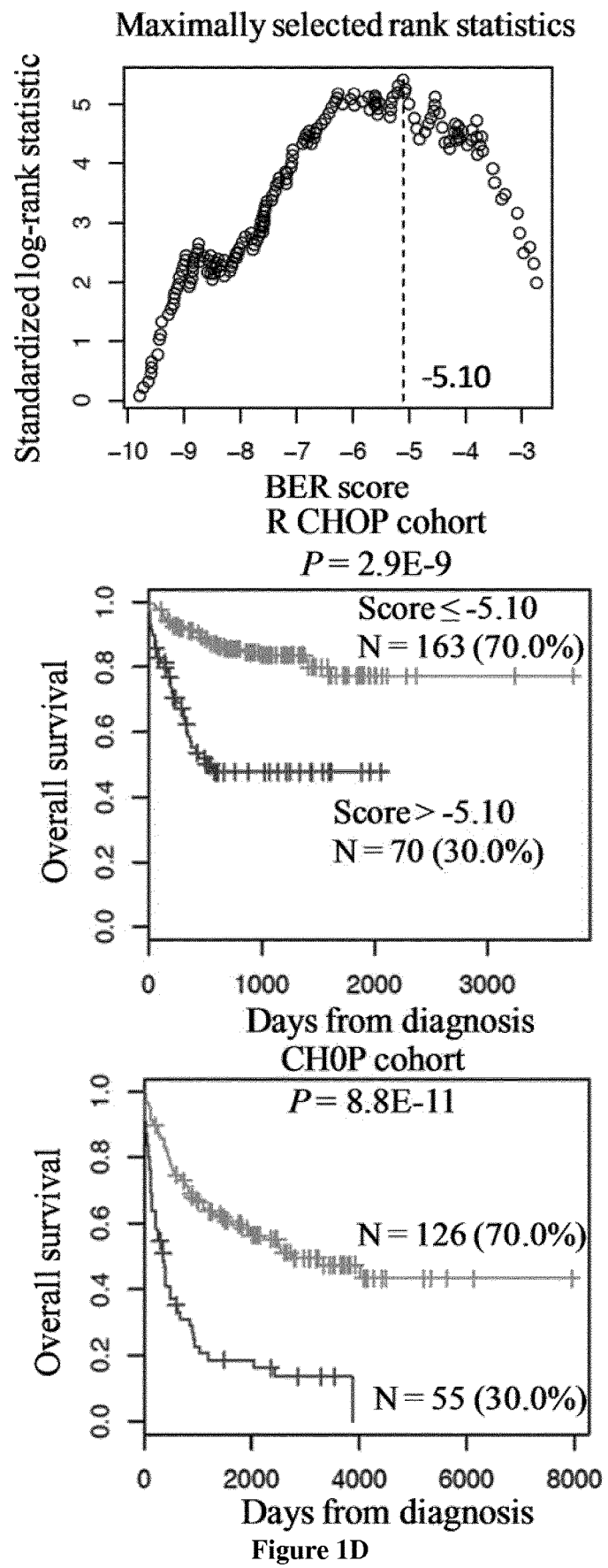
Figure 1E:
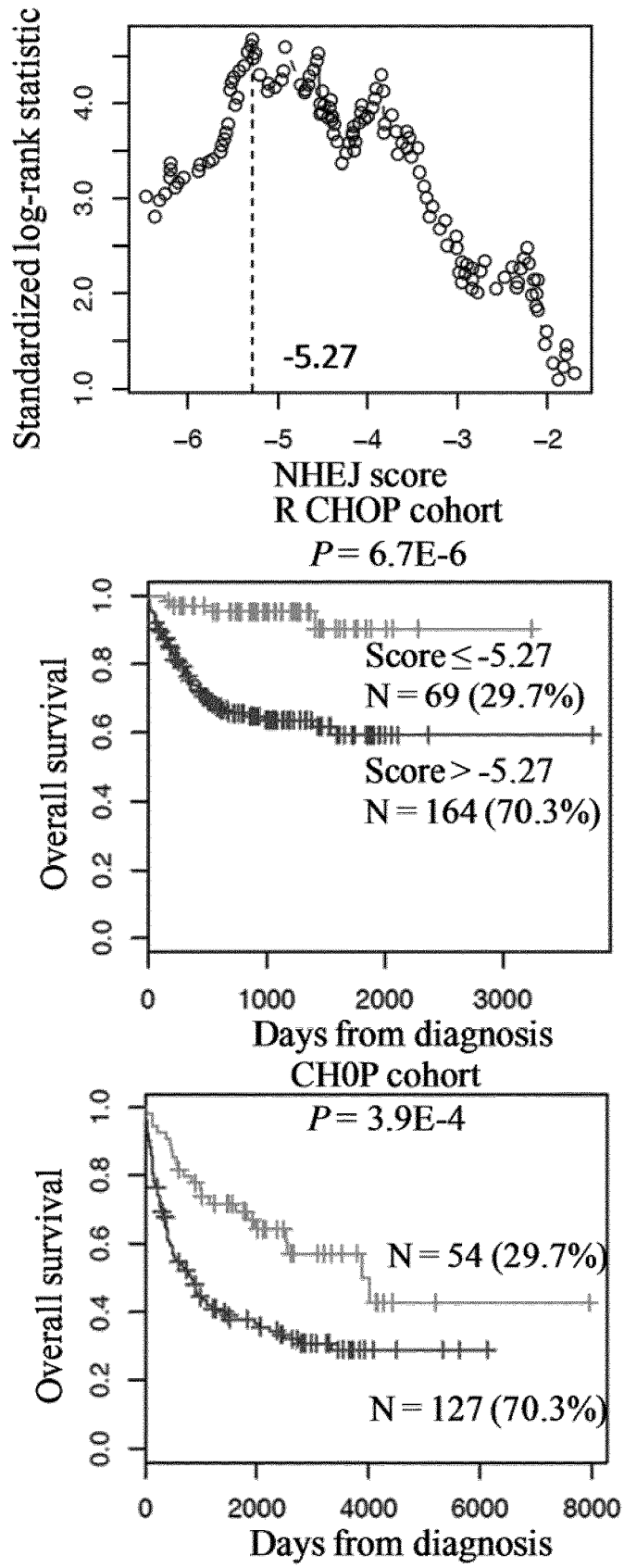

$$DNARS = \sum_{i=1}^{n} \beta i \times Ci \quad (I)$$

10 Claims, 16 Drawing Sheets

(51) Int. Cl.
| | |
|---|---|
| *G16B 20/00* | (2019.01) |
| *G16H 50/30* | (2018.01) |
| *G16B 25/00* | (2019.01) |
| *G16B 40/00* | (2019.01) |

(52) U.S. Cl.
CPC . *C12Q 2600/106* (2013.01); *C12Q 2600/158* (2013.01); *G16B 25/00* (2019.02); *G16B 40/00* (2019.02)

(56) References Cited

U.S. PATENT DOCUMENTS

2015/0275305 A1    10/2015  Moreaux et al.
2016/0152985 A1     6/2016  D'Andrea et al.

OTHER PUBLICATIONS

Prevo et al., "The novel ATR inhibitor VE-821 increases sensitivity of pancreatic cancer cells to radiation and chemotherapy", Cancer Biology & Therapy, 2012, pp. 1072-1081, vol. 13, No. 11.
Charrier et al., "Discovery of Potent and Selective Inhibitors of Ataxia Telangiectasia Mutated and Rad3 Related (ATR) Protein Kinase as Potential Anticancer Agents", Journal of Medicinal Chemistry, 2011, pp. 2320-2330, vol. 54.
Toledo et al., "A cell-based screen identifies ATR inhibitors with synthetic lethal properties for cancer-associated mutations", Nature Structural & Molecular Biology, 2011, pp. 721-727, vol. 18, No. 6.
Leahy et al., "Identification of a highly potent and selective DNA-dependent protein kinase (DNA-PK) inhibitor (NU7441) by screening of chromenone libraries", Bioorganic & Medicinal Chemistry Letters, 2004, pp. 6083-6087, vol. 14.
Zhao et al., "Preclinical Evaluation of a Potent Novel DNA-Dependent Protein Kinase Inhibitor NU7441", Cancer Research, 2006, pp. 5354-5362, vol. 66, No. 10.
Veuger et al., "Radiosensitization and DNA Repair Inhibition by the Combined Use of Novel Inhibitors of DNA-dependent Protein Kinase and Poly(ADP-Ribose) Polymerase-1", Cancer Research, 2003, pp. 6008-6015.
Willmore et al., "A novel DNA-dependent protein kinase inhibitor, NU7026, potentiates the cytotoxicity of topoisomerase II poisons used in the treatment of leukemia", Blood, 2004, pp. 4659-4665, vol. 103, No. 12.
Munck et al., "Chemosensitization of Cancer Cells by KU-0060648, a Dual Inhibitor of DNA-PK and PI-3K", Molecular Cancer Therapeutics, 2012, pp. 1789-1798, vol. 11, No. 8.
Rainey et al., "Transient Inhibition of ATM Kinase Is Sufficient to Enhance Cellular Sensitivity to Ionizing Radiation", Cancer Research, 2008, pp. 7466-7474, vol. 68, No. 18.
Tang et al., "Poly(ADP-ribose) Polymerase 1 Modulates the Lethality of CHK1 Inhibitors in Mammary Tumors", Molecular Pharmacology, 2012, pp. 322-332, vol. 82, No. 2.
Brezak et al., "IRC-083864, a novel bis quinone inhibitor of CDC25 phosphatases active against human cancer cells", International Journal of Cancer, 2009, pp. 1449-1456, vol. 124.
Ying et al., "Mre11-Dependent Degradation of Stalled DNA Replication Forks Is Prevented by BRCA2 and PARP1", Cancer Research, 2012, pp. 2814-2821, vol. 72, No. 11.
Neher et al., "Novel Irreversible Small Molecule Inhibitors of Replication Protein A Display Single-Agent Activity and Synergize with Cisplatin", Molecular Cancer Therapeutics, 2011, pp. 1796-1806, vol. 10, No. 10.
Huang et al., "Inhibition of Homologous Recombination in Human Cells by Targeting RAD51 Recombinase", Journal of Medicinal Chemistry, 2012, pp. 3011-3020, vol. 55.
Budke et al., "RI-1: a chemical inhibitor of RAD51 that disrupts homologous recombination in human cells", Nucleic Acids Research, 2012, pp. 7347-7357, vol. 40, No. 15.
Shaheen et al., "Synthetic lethality: exploiting the addiction of cancer to DNA repair", Blood, 2011, pp. 6074-6082, vol. 117, No. 23.
Sabharwal et al., "A phase I trial of lomeguatrib and irinotecan in metastatic colorectal cancer", Cancer Chemotherapy and Pharmacology, 2010, pp. 829-835, vol. 66.
Derenzini et al., "Constitutive activation of the DNA damage response pathway as a novel therapeutic target in diffuse large B-cell lymphoma", Oncotarget, 2015, vol. 6, No. 9.
Shah et al., "PARP inhibitors in cancer therapy: magic bullets but moving targets", Frontiers in Oncology, 2013, Article 279, vol. 3.
International Search Report, dated Oct. 20, 2015, from corresponding PCT application No. PCT/EP2015/067174.
European Office Action, dated Apr. 23, 2018, from corresponding EP Application No. 15 741 568.8.
G. Lenz et al., Affymetrix gene expression data (HG-U133 plus 2.0 microarrays), Gene Expression Omnibus (http://ncbi.nlm.nih.gov/geo/), submission date: Mar. 14, 2008, accession No. GSE10846.
Jung et al., "Mechanism and Control of V(D)J Recombination at the Immunoglobulin Heavy Chain Locus", Annual Review of Immunology, 2006, vol. 24, pp. 541-570.
Kotnis et al., "Non-homologous end joining in class switch recombination: the beginning of the end", Philosophical Transactions of The Royal Society of London, Series B, Biological Sciences, 2009, pp. 653-665, vol. 364.
Di Noia et al., "Molecular Mechanisms of Antibody Somatic Hypermutation", Annual Review of Biochemistry, 2007, pp. 1-22, vol. 76.
Stavnezer et al., "Mapping of Switch Recombination Junctions, a Tool for Studying DNA Repair Pathways during Immunoglobulin Class Switching", Advances in Immunology, 2010, pp. 45-109, vol. 108.
Chiarle et al., "Translocations in Normal B Cells and Cancers: Insights from New Technical Approaches", Advances in Immunology, 2013, pp. 39-71, vol. 117.
Siegel et al., "Cancer Statistics, 2012", CA: A Cancer Journal for Clinicians, 2012, pp. 10-29, vol. 62.
Staudt et al., "The Biology of Human Lymphoid Malignancies Revealed by Gene Expression Profiling", Advances in Immunology, 2005, pp. 163-208, vol. 87.
Lenz et al., "Aggressive Lymphomas", The New England Journal of Medicine, 2010, pp. 1417-1429, vol. 362.
Lenz et al., "Stromal Gene Signatures in Large-B-Cell Lymphomas", The New England Journal of Medicine, 2008, pp. 2313-2323, vol. 359, No. 22.
Rosenwald et al., "The Use of Molecular Profiling to Predict Survival After Chemotherapy for Diffuse Large-B-Cell Lymphoma", The New England Journal of Medicine, 2002, pp. 1937-1947, vol. 346, No. 25.
Wright et al., "A gene expression-based method to diagnose clinically distinct subgroups of diffuse large B cell lymphoma", Proceedings of the National Academy of Sciences of the United States of America, 2003, pp. 9991-9996, vol. 100, No. 17.
Noel FCC de Miranda et al., "DNA repair genes are selectively mutated in diffuse large B cell lymphomas", The Journal of Experimental Medicine, 2013, pp. 1729-1742, vol. 210, No. 9.
Luo et al., "Principles of Cancer Therapy: Oncogene and Non-oncogene Addiction", Cell, 2009, pp. 823-837, vol. 136, No. 5.
Kennedy et al., "DNA Repair Pathways in Clinical Practice: Lessons From Pediatric Cancer Susceptibility Syndromes", Journal of Clinical Oncology, 2006, pp. 3799-3808, vol. 24, No. 23.
Savitsky et al., "A Single Ataxia Telangiectasia Gene with a Product Similar to PI-3 Kinase", Science, 1995, pp. 1749-1753, vol. 268.
McKinnon et al., "DNA Strand Break Repair and Human Genetic Disease", Annual Review of Genomics and Human Genetics, 2007, pp. 37-55, vol. 8.
Futreal et al., "BRCA1 Mutations in Primary Breast and Ovarian Carcinomas", Sciences, 1994, pp. 120-122, vol. 266.
Wooster et al., "Identification of the breast cancer susceptibility gene BRCA2", Nature, 1995, pp. 789-792, vol. 378, No. 21/28.
Bret et al., "Gene expression-based risk score in diffuse large B-cell lymphoma", Oncotarget, 2012, pp. 1700-1710, vol. 3, No. 12.

(56) References Cited

OTHER PUBLICATIONS

Bret et al., "Nucleotide excision DNA repair pathway as a therapeutic target in patients with high-risk diffuse large B cell lymphoma", Cell Cycle, 2013, vol. 12, No. 12.
Gentleman et al., "Bioconductor: open software development for computational biology and bioinformatics", Genome Biology, 2004, Article R80, vol. 5, No. 10.
Vastrik et al., "Reactome: a knowledge base of biologic pathways and processes", Genome Biology, 2007, Article R39, vol. 8, No. 3.
Milanowska et al., "REPAIRtoire—a database of DNA repair pathways", Nucleic Acids Research, 2011, pp. D788-D792, vol. 39.
Samra et al., "Development of gene expression-based risk score in cytogenetically normal acute myeloid leukemia patients", Oncotarget, 2012, pp. 824-832, vol. 3, No. 8.
Kassambara et al., "Genes with a spike expression are clustered in chromosome (sub)bands and spike (sub)bands have a powerful prognostic value in patients with multiple myeloma", Haematologica, 2012, pp. 622-630, vol. 97, No. 4.
Subramaniana et al., "Gene set enrichment analysis: A knowledge-based approach for interpreting genome-wide expression profiles", Proceedings of the National Academy of Sciences of the United States of America, 2005, pp. 15545-15550, vol. 102, No. 43.
Klein et al., "Germinal centres: role in B-cell physiology and malignancy", Nature Reviews: Immunology, 2008, pp. 22-33, vol. 8.
Lenz et al., "Aberrant immunoglobulin class switch recombination and switch translocations in activated B cell—like diff use large B cell lymphoma", The Journal of Experimental Medicine, 2007, pp. 633-643, vol. 204, No. 3.
Chen et al., "The Fanconi anemia (FA) pathway confers glioma resistance to DNA alkylating agents", Journal of Molecular Medicine, 2007, pp. 497-509, vol. 85, No. 5.
Taniguchi et al., "Disruption of the Fanconi anemia—BRCA pathway in cisplatin-sensitive ovarian tumors", Nature Medicine, 2003, pp. 568-574, vol. 9, No. 5.
Helleday, "Homologous recombination in cancer development, treatment and development of drug resistance", Carcinogenesis, 2010, pp. 955-960, vol. 31, No. 6.
Curtin et al., "Inhibiting the DNA damage response as a therapeutic manoeuvre in cancer", British Journal of Pharmacology, 2013, pp. 1745-1765, vol. 169.
Ferrao et al., "Efficacy of CHK inhibitors as single agents in MYC-driven lymphoma cells", Oncogene, 2012, pp. 1661-1672, vol. 31.
Yoon et al., "MYC translocation and an increased copy number predict poor prognosis in adult diffuse large B-cell lymphoma (DLBCL), especially in germinal centre-like B cell (GCB) type", Histopathology, 2008, pp. 205-217, vol. 53.
Klapper et al., "Structural aberrations affecting the MYC locus indicate a poor prognosis independent of clinical risk factors in diffuse large B-cell lymphomas treated within randomized trials of the German High-Grade Non-Hodgkin's Lymphoma Study Group (DSHNHL)", Leukemia, 2008, pp. 2226-2229, vol. 22.
Barrans et al., "Rearrangement of MYC Is Associated With Poor Prognosis in Patients With Diffuse Large B-Cell Lymphoma Treated in the Era of Rituximab", Journal of Clinical Oncology, 2010, pp. 3360-3365, vol. 28, No. 20.
Savage et al., "MYC gene rearrangements are associated with a poor prognosis in diffuse large B-cell lymphoma patients treated with R-CHOP chemotherapy", Blood, 2009, pp. 3533-3537, vol. 114, No. 17.
Leucci et al., "MYC translocation-negative classical Burkitt lymphoma cases: an alternative pathogenetic mechanism involving miRNA deregulation", Journal of Pathology, 2008, pp. 440-450, vol. 216.
Onnis et al., "Alteration of MicroRNAs Regulated by c-Myc in Burkitt Lymphoma", PLoS One, 2010, Article e12960, vol. 5, No. 9.
Stasik et al., "Increased MYC gene copy number correlates with increased mRNA levels in diffuse large B-cell lymphoma", Haematologica, 2010, pp. 597-603, vol. 95, No. 4.
Chapuy et al., "Discovery and Characterization of Super-Enhancer Associated Dependencies in Diffuse Large B-Cell Lymphoma", Cancer Cell, 2013, pp. 777-790, vol. 24, No. 6.
Curtin., "DNA repair dysregulation from cancer driver to therapeutic target", Nature Reviews Cancer, 2012, pp. 801-817, vol. 12.
Jiang et al., "Deep sequencing reveals clonal evolution patterns and mutation events associated with relapse in B-cell lymphomas", Genome Biology, 2014, vol. 15, No. 432.
Hickson et al., "Identification and Characterization of a Novel and Specific Inhibitor of the Ataxia-Telangiectasia Mutated Kinase ATM", Cancer Research, 2004, pp. 9152-9159, vol. 64, No. 24.
Li et al., "The ATM Inhibitor KU-55933 Suppresses Cell Proliferation and Induces Apoptosis by Blocking Akt in Cancer Cells with Overactivated Akt", Molecular Cancer Therapeutics, 2010, pp. 113-125, vol. 9, No. 1.
Golding et al., "Improved ATM kinase inhibitor KU-60019 radiosensitizes glioma cells, compromises insulin, AKT and ERK prosurvival signaling, and inhibits migration and invasion", Molecular Cancer Therapeutics, 2009, pp. 2894-2902, vol. 8, No. 10.
Peaslan et al., "Identification and evaluation of a potent novel ATR inhibitor, NU6027, in breast and ovarian cancer cell lines", British Journal of Cancer, 2011, pp. 372-381, vol. 105.
Reaper et al., "Selective killing of ATM- or p53-deficient cancer cells through inhibition of ATR", Nature Chemical Biology, 2011, vol. 7, No. 7, pp. 428-430.

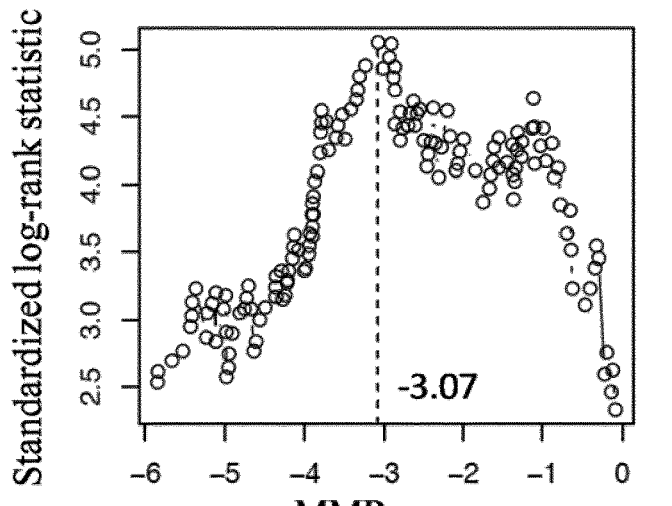
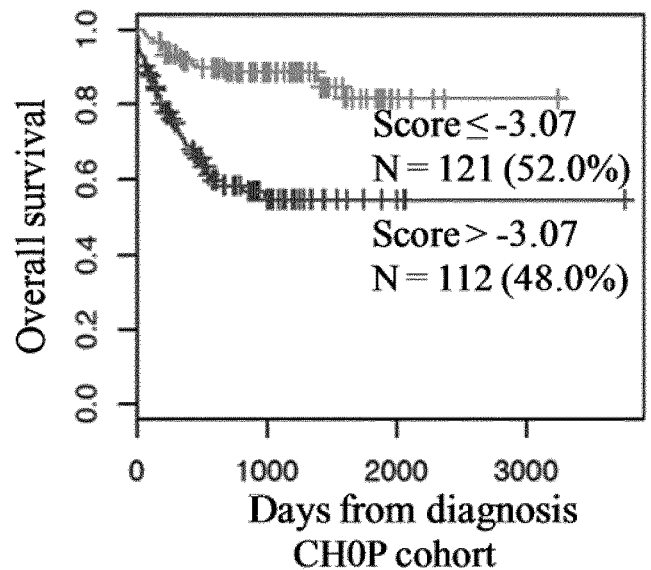
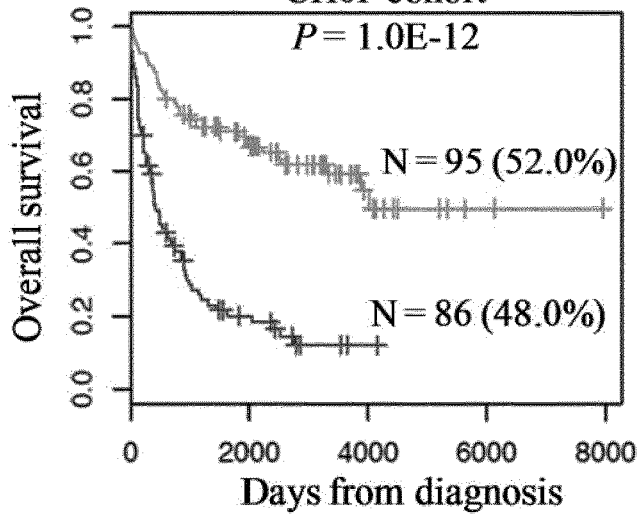
Figure 1F

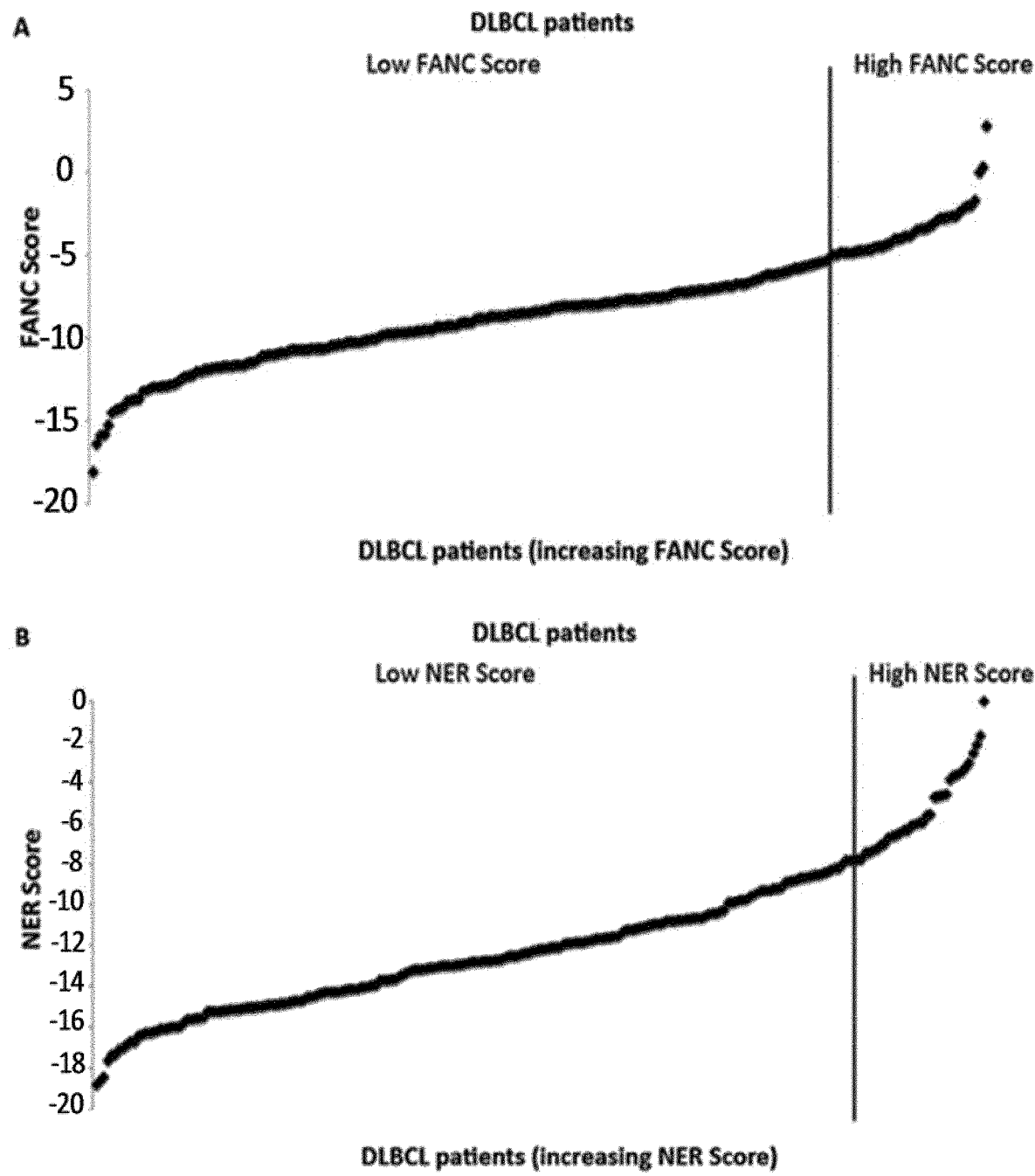
Figure 6 A and B

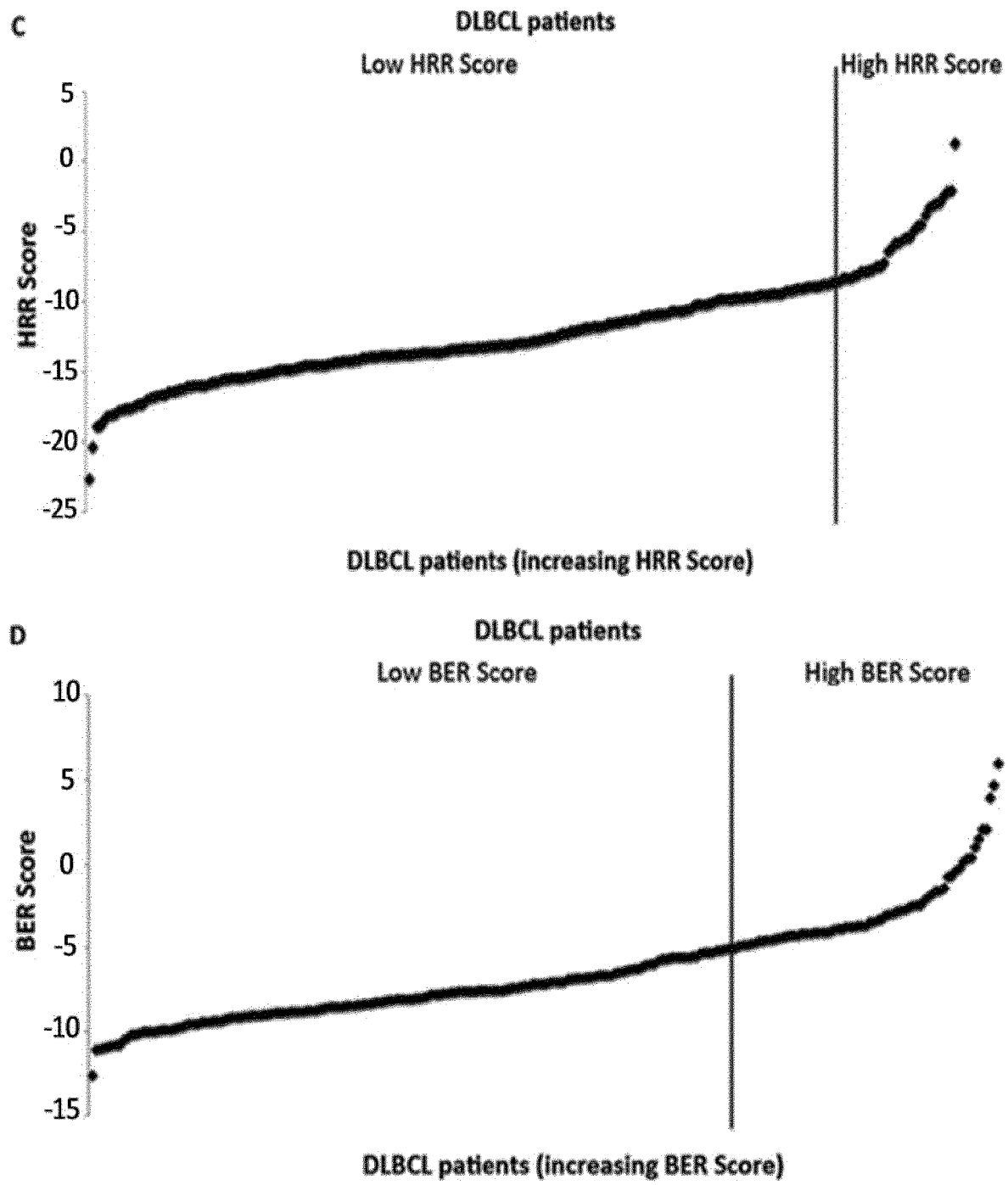
Figure 6 C and D

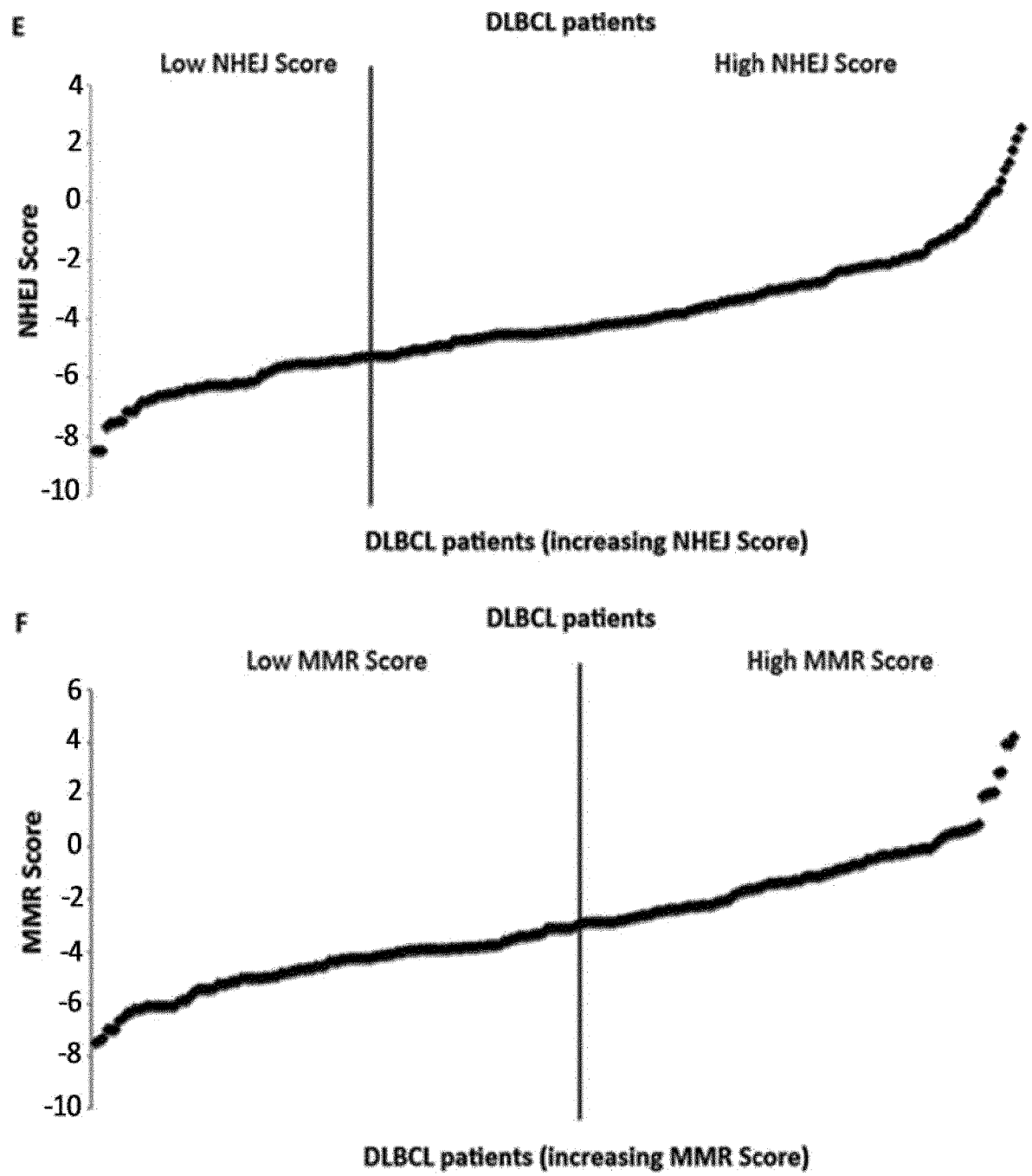
Figure 6 E and F

METHODS FOR PREDICTING RESPONSE TO DNA REPAIR PATHWAY INHIBITORS IN DIFFUSE LARGE B-CELL LYMPHOMA

FIELD OF THE INVENTION

The present invention relates to methods for predicting diffuse large B-cell lymphoma treatment response.

BACKGROUND OF THE INVENTION

The generation of B lymphocytes involves DNA breaks, recombination of variable (V), diversity (D) and joining (J) segments into the immunoglobulin variable region exons, somatic hypermutation and class switch recombination (1). Double strand DNA breaks are induced by the activity of the recombination activating proteins 1 and 2 (RAG1, RAG2) and are repaired by the non-homologous end joining pathway (NHEJ) (2). Guanosine-uracil mismatches are generated by activation-induced cytidine deaminase (AID) and are processed by the base excision repair pathway (BER) and the mismatch repair pathway (MMR) (3,4). These DNA lesions, if improperly repaired, may lead to genetic instability and chromosomal translocations in B lymphoid cells, and then to lymphomagenesis (5).

Diffuse large B-cell lymphoma (DLBCL) accounts for 30 to 40% of adult non-Hodgkin lymphomas (LNH). Most patients diagnosed with DLBCL achieve long-term remission after treatment, but a third of them relapse after conventional Rituximab (R)-based chemotherapy regimens such as combination of cyclophosphamide, doxorubicin, vincristine and prednisone (CHOP) (6). DLBCL is a heterogeneous disease both in term of clinical and biological presentation (7). Gene expression profiling (GEP) of the tumors has allowed the identification of three molecular subgroups associated with distinct genetic abnormalities, clinical behavior and responsiveness to therapy (8-11).

The germinal-center B-cell-like (GCB) subgroup accounts for 50% of DLBCL, is associated with a good outcome and tumor cells have a GEP close to that healthy germinal-center B cells. The activated B cell-like subtype (ABC) subgroup accounts for 30% of cases, has a poorer outcome and tumor cells have a healthy peripheral blood activated B cell GEP with a nuclear factor kappa B (NF-kB) signature. Using CHOP-like chemotherapy, the 5-year overall survival rates of patients with GCB signature and of patients with ABC profile are 60% and 30% respectively (11). The third subtype, primary mediastinal B cell lymphoma (PMBL), accounts for 20% of cases, displays a mediastinal presentation and a GEP closed to that of Hodgkin's lymphoma, but with genes characteristic of mature B cells (10).

Distinct oncogenic pathways have been identified in DLBCL molecular subtypes as reviewed by Lenz et al (8). Some of them are linked with genomic instability as TP53 mutation, MDM2 gain or amplification, PTEN and ING1 deletion in the GCB subgroup or INK4A-ARF deletion in the ABC subgroup. Aberrant DNA repairs are likely a cause of DLBCL lymphomagenesis (12). Somatic and germline mutations in non Ig genes linked with the mismatch repair or non homologous end-joining pathways have been identified (12).

Tumorigenesis was described as a disease of DNA repair since it has at origin DNA mutations linked to genomic instability (13,14). Mutations of DNA repair genes were shown to be involved in cancer transformation (15-18). However, DNA repair pathways are required in cancer cells to survive to chronic replication stress that impede the duplication of their genome and could lead to mitotic catastrophe (19). DNA repair represents therefore a double-edged sword in cancer. To overcome this antagonism, tumor cells will become addicted to DNA repair pathways different from the defective one involved in the initial neoplastic transformation. This addiction could represent the Achilles' heel of tumor cells and can be exploited therapeutically to hamper repair of the intrinsic DNA damages occurring during replication or to amplify the chemotherapy induced DNA damages (19). Selective mutations of DNA repair genes including mismatch repair (MMR) genes (EXO1, MSH2 and MSH6), non homologous end-joining (NHEJ) genes (DCLRE11C, PRKDC, XRCC5 and XRCC6), homologous recombination (HR) BRCA2 gene and nucleotide excision repair DDB1 gene were reported in DLBCL (12). Furthermore, DLBCL high-risk patients overexpressed genes coding for nucleotide excision DNA repair (NER) pathway, including ERCC2/XPD, ERCC3/XPB, ERCC4/XPF, ERCC6/CSB, ERCC8/CSA, DDB2 and polymerase delta that could be linked with resistance to CHOP-based regimens (20,21).

In the present invention, the inventors aimed to identify deregulated DNA repair pathways in DLBCL tumor samples in order to exploit the concept of synthetic lethality. There is no disclosure in the art of a method of testing whether a patient suffering of diffuse large B-cell lymphoma will respond or not to a DNA repair pathway inhibitor selected from FANC, NER, BER, NHEJ, MMR and HRR DNA repair pathway inhibitors.

SUMMARY OF THE INVENTION

The present invention relates to a method of testing whether a patient suffering of diffuse large B-cell lymphoma will respond or not to a DNA repair pathway inhibitor selected from FANC, NER, BER, NHEJ, MMR and HRR DNA repair pathway inhibitors.

DETAILED DESCRIPTION OF THE INVENTION

Diffuse large B-cell lymphoma (DLBCL) is the most common type of non-Hodgkin lymphoma and displays heterogeneous clinical and molecular characteristics. Every day, a healthy cell is faced with thousands of DNA damages, which have to be fixed by various DNA repair pathways. A deregulation of these pathways may yield to genetic instability, cancer, and confers resistance to DNA targeting drugs in cancer patients.

Therefore, inhibitors of DNA repair pathways may help overcoming drug resistance. In some cases, the defect in a given DNA repair pathways may render cancer cell survival dependent on a complementary pathway, which can be targeted to prompt cancer cell death.

In the present invention, high throughput gene expression profiling of DLBCL tumor samples was used to document the expression of genes coding for DNA repair pathways. The inventors designed DNA repair pathway scores predictive for overall survival in two cohorts of DLBCL patients. FANC score, BER score, NHEJ score and MMR score were shown to be an independent predictor for OS when compared to the previously published prognostic factors. When all DNA repair scores were tested together, FANC score, NHEJ score and MMR score remained significant. Interestingly, combining FANC, NHEJ and MMR scores in a DNA repair score led to a more potent prognostic classification of DLBCL patients. These DNA repair scores have a strong potential to identify high-risk DLBCL patients and exploit addiction to a specific DNA repair pathway in order to define the best DNA repair inhibitor to employ in combination with conventional treatment.

Definitions

The term "patient" denotes a mammal. In a preferred embodiment of the invention, a patient refers to any patient (preferably human) afflicted with diffuse large B-cell lymphoma. In another preferred embodiment of the invention, the term "patient" refers to a patient suffering of diffuse large B-cell lymphoma receiving a diffuse large B-cell lymphoma treatment. In another preferred embodiment, the patient suffering of diffuse large B-cell lymphoma is resistant to the diffuse large B-cell lymphoma treatment.

The term "diffuse large B-cell lymphoma" refers to diffuse large B-cell lymphoma such as revised in the World Health Organisation Classification C83.3.

The term "diffuse large B-cell lymphoma treatment" refers to anthracycline-based chemotherapy regimens such as a combination of cyclophosphamide, doxorubicin, vincristine, and prednisone (CHOP) and Rituximab-CHOP chemotherapy regimens (R-CHOP).

The term "DNA repair pathway inhibitor" has its general meaning in the art and refers to a diffuse large B-cell lymphoma treatment. The term "DNA repair pathway inhibitor" refers to DNA repair pathway inhibitor selected from FANC (Fanconi anemia) inhibitors, NER (nucleotide excision repair) inhibitors, BER (base excision repair) inhibitors, NHEJ (non-homologous end-joining) inhibitors, MMR (mismatch repair) inhibitors and HRR (homologous recombination repair) inhibitors. The term "DNA repair pathway inhibitor" also refers to compounds which inhibit the ability of the DNA repair pathway to repair DNA damage.

The term "FANC inhibitor" has its general meaning in the art and refers to FANC DNA repair pathway inhibitors such as compounds described in WO2008066624, U.S. Pat. No. 7,858,331, and inhibitors of FANCD2 monoubiquitylation such as proteasome inhibitors bortezomib and MG132, curcumin, and the curcumin analogs EF24 and 4H-TTD.

The term "NER inhibitor" has its general meaning in the art and refers to NER DNA repair pathway inhibitors such as F11782 (Bret et al., 2013), Cyclosporine, and Cetuximab.

The term "BER inhibitor" has its general meaning in the art and refers to BER DNA repair pathway inhibitors such as TRC102 (21), Iniparib (21), ABT-888 (also known as veliparib) (21), AZD2281 (also known as olaparib) (21), CEP-8933 (21), INO-1001 (21), AG014699 (21), GPI21016 (also known as E7016) (21), MK4827 (21), NSC-281680, Pamoic acid, oleanolic acid and eicosapentaenoic acid, L67 and L189, Methoxyamine, Lucanthone, CRT0044876, AG014688 (also known as CO-338 and rucaparib), CEP-9722, BMN673, and BSI-201 (also known as iniparib). The term "BER inhibitor" also refers to PARP inhibitors such as inhibitor of poly(ADP-ribose) polymerase-1 (PARP-1) PJ34 hydrochloride, Iniparib, Veliparib, Olaparib, CEP-8933, INO-1001, AG014699, GPI21016 and MK4827.

The term "NHEJ inhibitor" has its general meaning in the art and refers to NHEJ DNA repair pathway inhibitors such as NU-7441 (9, 10), NU-7026 (11, 12), Iniparib (21), Veliparib (21), Olaparib (21), CEP-8933 (21), INO-1001 (21), AG014699 (21), GPI21016 (21), MK4827 (21), NU7026, NU7441, IC86621 and IC87361, OK-135, SU11752, and CC-115.

The term "MMR inhibitor" has its general meaning in the art and refers to MMR DNA repair pathway inhibitors such as Lomeguatrib (21, 22), 06-benzylguanine (21), and DAC.

The term "HRR inhibitor" has its general meaning in the art and refers to HRR DNA repair pathway inhibitors such as MCI13E (18), B02 (19), RI-1 (20), Mirin, B02, A03, A10 and imatinib, AG024322 and SCH727965 (CDK1 inhibitors).

The term "biological sample" refers to diffuse large B-cell lymphoma cells, blood, serum, or plasma.

All the genes pertaining to the invention are known per se, and are listed in the below Tables A, B, C, D, E, F and G.

TABLE A

Identification of Fanconi (FANC) pathway genes whose expression associated with a prognostic value in DLBCL patients. Fanconi DNA repair pathway score (FANC DNARS) genes.

| UNIQID | Name | Beta coefficient | HR | Prognostic value | Reference Level (ELRi) | Reference Level (ELRi) Percentage in patients' cohort | Benjamini Hochberg corrected p value |
|---|---|---|---|---|---|---|---|
| 220255_at | FANCE | 0.993790143 | 2.70 | BAD | 198 | 89.85 | 1.0E−2 |
| 242804_at | POLN | 0.894544042 | 2.44 | BAD | 24 | 89.13 | 2.1E−2 |
| 218317_x_at | SLX1 | 0.834709914 | 2.30 | BAD | 859 | 67.39 | 4.6E−5 |
| 203564_at | FANCG | 0.826646149 | 2.28 | BAD | 1429 | 17.87 | 3.8E−5 |
| 65591_at | WDR48 | 0.7636288 | 2.14 | BAD | 990 | 10.14 | 2.4E−4 |
| 1552937_s_at | ATRIP | 0.761522676 | 2.14 | BAD | 759 | 15.21 | 8.4E−4 |
| 214299_at | TOP3A | 0.687124458 | 1.99 | BAD | 338 | 30.19 | 2.1E−4 |
| 213008_at | FANCI | 0.681798555 | 1.98 | BAD | 509 | 89.61 | 4.9E−2 |
| 203229_s_at | CLK2 | 0.673454119 | 1.96 | BAD | 2246 | 46.61 | 3.7E−4 |
| 221800_s_at | C17orf70/FAAP100 | 0.626604357 | 1.87 | BAD | 578 | 41.54 | 4.9E−4 |
| 235215_at | ERCC4 | 0.619519753 | 1.86 | BAD | 617 | 12.31 | 5.0E−3 |
| 223545_at | FANCD2 | 0.593972707 | 1.81 | BAD | 322 | 54.34 | 1.7E−3 |
| 203678_at | FAN1 | 0.592337616 | 1.81 | BAD | 400 | 69.56 | 6.1E−3 |
| 203805_s_at | FANCA | 0.571168788 | 1.77 | BAD | 1250 | 29.46 | 1.4E−3 |
| 201756_at | RPA2 | 0.564240535 | 1.76 | BAD | 3573 | 23.18 | 2.2E−3 |
| 205189_s_at | FANCC | 0.559293676 | 1.75 | BAD | 473 | 24.87 | 2.1E−3 |
| 221206_at | PMS2 | 0.541332725 | 1.72 | BAD | 985 | 35.02 | 2.1E−3 |

TABLE A-continued

Identification of Fanconi (FANC) pathway genes whose expression associated with a prognostic value in DLBCL patients. Fanconi DNA repair pathway score (FANC DNARS) genes.

| UNIQID | Name | Beta coefficient | HR | Prognostic value | Reference Level (ELRi) | Reference Level (ELRi) Percentage in patients' cohort | Benjamini Hochberg corrected p value |
|---|---|---|---|---|---|---|---|
| 201529_s_at | RPA1 | 0.533510226 | 1.70 | BAD | 3026 | 34.54 | 2.3E−3 |
| 205394_at | CHEK1 | 0.528159908 | 1.69 | BAD | 1541 | 13.52 | 1.6E−2 |
| 222713_s_at | FANCF | 0.516794711 | 1.67 | BAD | 669 | 17.14 | 1.3E−2 |
| 214727_at | BRCA2 | 0.51043993 | 1.66 | BAD | 324 | 10.14 | 2.7E−2 |
| 208442_s_at | ATM | 0.499720498 | 1.65 | BAD | 357 | 55.31 | 7.6E−3 |
| 218428_s_at | REV1 | 0.487390595 | 1.63 | BAD | 1095 | 62.07 | 1.1E−2 |
| 234464_s_at | EME1 | 0.481989713 | 1.62 | BAD | 687 | 70.53 | 2.0E−2 |
| 214816_x_at | C19orf40/ FAAP24 | 0.480973838 | 1.62 | BAD | 220 | 65.21 | 1.7E−2 |
| 218463_s_at | MUS81 | 0.47906345 | 1.61 | BAD | 1353 | 49.51 | 7.1E−3 |
| 202520_s_at | MLH1 | 0.469484016 | 1.60 | BAD | 3167 | 71.01 | 2.2E−2 |
| 205024_s_at | RAD51 | 0.44358785 | 1.56 | BAD | 1352 | 28.98 | 1.3E−2 |
| 233852_at | POLH | 0.430217571 | 1.54 | BAD | 642 | 31.15 | 1.4E−2 |
| 219317_at | POLI | 0.398668422 | 1.49 | BAD | 424 | 54.58 | 2.4E−2 |
| 209507_at | RPA3 | −0.539724756 | 0.58 | GOOD | 5753 | 49.27 | 2.8E−3 |
| 1557217_a_at | FANCB | −0.561972725 | 0.57 | GOOD | 24 | 77.29 | 2.4E−3 |
| 202412_s_at | USP1 | −0.661144729 | 0.52 | GOOD | 1146 | 54.83 | 4.5E−4 |

TABLE B

Identification of nucleotide excision repair (NER) genes whose expression associated with a prognostic value in DLBCL patients. NER DNARS genes.

| UNIQID | Name | Beta coefficient | HR | Prognostic value | Reference Level (ELRi) | Reference Level (ELRi) Percentage in patients' cohort | Benjamini Hochberg corrected p value |
|---|---|---|---|---|---|---|---|
| 203422_at | POLD1 | 0.937222702 | 2.55 | BAD | 1732 | 12.08 | 5.2E−5 |
| 207348_s_at | LIG3 | 0.781143939 | 2.18 | BAD | 229 | 34.30 | 5.1E−5 |
| 202167_s_at | MMS19 | 0.720845763 | 2.05 | BAD | 1523 | 19.81 | 2.4E−4 |
| 213468_at | ERCC2 | 0.675424597 | 1.96 | BAD | 240 | 44.69 | 2.5E4 |
| 201423_s_at | CUL4A | 0.651624653 | 1.92 | BAD | 1480 | 26.33 | 3.6E−4 |
| 233893_s_at | UVSSA | 0.640314432 | 1.90 | BAD | 662 | 47.83 | 7.0E−4 |
| 203577_at | GTF2H4/ TFIIH4 | 0.632740034 | 1.88 | BAD | 407 | 63.04 | 1.5E−3 |
| 202726_at | LIG1 | 0.624320566 | 1.87 | BAD | 1038 | 45.89 | 7.2E−4 |
| 205162_at | ERCC8 | 0.623186964 | 1.86 | BAD | 397 | 48.07 | 6.9E−4 |
| 235215_at | ERCC4 | 0.619519753 | 1.86 | BAD | 617 | 12.32 | 5.0E−3 |
| 201046_s_at | RAD23A | 0.605949784 | 1.83 | BAD | 4507 | 21.50 | 1.4E−3 |
| 218110_at | XAB2 | 0.5675841 | 1.76 | BAD | 339 | 33.82 | 1.3E−3 |
| 201756_at | RPA2 | 0.564240535 | 1.76 | BAD | 3573 | 23.19 | 2.3E−3 |
| 205672_at | XPA | 0.5395648 | 1.71 | BAD | 774 | 71.50 | 1.1E−2 |
| 201529_s_at | RPA1 | 0.533510226 | 1.70 | BAD | 3026 | 34.54 | 2.4E−3 |
| 216026_s_at | POLE | 0.517879065 | 1.68 | BAD | 486 | 62.32 | 8.3E−3 |
| 201222_s_at | RAD23B | 0.490819009 | 1.63 | BAD | 5821 | 20.29 | 1.3E_2 |
| 208619_at | DDB1 | 0.485175633 | 1.62 | BAD | 4243 | 53.62 | 7.7E−3 |
| 202176_at | ERCC3 | 0.415448239 | 1.51 | BAD | 671 | 51.93 | 2.2E−2 |
| 201202_at | PCNA | −0.410969369 | 0.66 | GOOD | 9365 | 51.45 | 1.9E−2 |
| 203565_s_at | MNAT1 | −0.431668929 | 0.65 | GOOD | 616 | 37.44 | 2.2E−2 |
| 202451_at | GTF2H1/ TFIIH1 | −0.460173497 | 0.63 | GOOD | 1520 | 78.99 | 1.3E−2 |
| 213357_at | GTF2H5/ TFIIH5 | −0.471509813 | 0.62 | GOOD | 2494 | 66.91 | 6.9E−3 |
| 209375_at | XPC | −0.471837049 | 0.62 | GOOD | 1073 | 79.23 | 1.3E−2 |
| 204093_at | CCNH | −0.473982179 | 0.62 | GOOD | 2674 | 55.31 | 6.4E−3 |
| 218117_at | RBX1 | −0.522774731 | 0.59 | GOOD | 5431 | 79.47 | 6.4E−3 |
| 209507_at | RPA3 | −0.539724756 | 0.58 | GOOD | 5753 | 49.28 | 2.8E−3 |
| 209194_at | CETN2 | −0.578808294 | 0.56 | GOOD | 1055 | 86.47 | 6.4E−3 |
| 202414_at | ERCC5 | −0.73980651 | 0.48 | GOOD | 1414 | 23.67 | 4.1E−3 |

TABLE C

Identification of base excision repair (BER) genes whose expression associated with a prognostic value in DLBCL patients. BER DNARS genes.

| UNIQID | Name | Beta coefficient | HR | Prognostic value | Reference Level (ELRi) | Reference Level (ELRi) Percentage in patients' cohort | Benjamini Hochberg corrected p value |
|---|---|---|---|---|---|---|---|
| 203422_at | POLD1 | 0.9372227 | 2.55 | BAD | 1732 | 12.08 | 5.2E-5 |
| 207348_s_at | LIG3 | 0.7811439 | 2.18 | BAD | 229 | 34.30 | 5.1E-5 |
| 209731_at | NTHL1 | 0.7772735 | 2.17 | BAD | 560 | 12.80 | 3.3E-4 |
| 201115_at | POLD2 | 0.7457501 | 2.11 | BAD | 1006 | 64.49 | 5.3E-4 |
| 218527_at | APTX | 0.7305743 | 2.07 | BAD | 1166 | 29.95 | 1.3E-4 |
| 207727_s_at | MUTYH | 0.7302693 | 2.07 | BAD | 1404 | 36.71 | 1.2E-4 |
| 218961_s_at | PNKP | 0.7272944 | 2.06 | BAD | 958 | 35.02 | 1.1E-4 |
| 204408_at | APEX2 | 0.7152181 | 2.04 | BAD | 422 | 78.74 | 6.4E-3 |
| 215773_x_at | PARP2 | 0.6514674 | 1.92 | BAD | 1925 | 11.59 | 4.1E-3 |
| 226585_at | NEIL2 | 0.6412682 | 1.89 | BAD | 300 | 25.36 | 5.0E-4 |
| 202726_at | LIG1 | 0.6243206 | 1.86 | BAD | 1038 | 45.89 | 7.2E-4 |
| 216026_s_at | POLE | 0.5178791 | 1.68 | BAD | 486 | 62.32 | 8.2E-3 |
| 219502_at | NEIL3 | 0.5036950 | 1.65 | BAD | 288 | 59.42 | 8.3E-3 |
| 221049_s_at | POLL | 0.4698094 | 1.60 | BAD | 58 | 80.43 | 4.7E-2 |
| 202330_s_at | UNG | 0.4671505 | 1.59 | BAD | 2120 | 23.91 | 1.1E-2 |
| 203655_at | XRCC1 | 0.4370908 | 1.55 | BAD | 576 | 48.31 | 1.2E-2 |
| 233852_at | POLH | 0.4302176 | 1.54 | BAD | 642 | 31.16 | 1.4E-2 |
| 210027_s_at | APEX1 | 0.3919936 | 1.48 | BAD | 6822 | 67.39 | 3.9E-2 |
| 201202_at | PCNA | -0.4109694 | 0.66 | GOOD | 9365 | 51.45 | 1.9E-2 |
| 202996_at | POLD4 | -0.4154167 | 0.66 | GOOD | 1701 | 58.94 | 1.5E-2 |
| 219396_s_at | NEIL1 | -0.4640568 | 0.63 | GOOD | 353 | 52.66 | 7.5E-3 |
| 205301_s_at | OGG1 | -0.5326244 | 0.59 | GOOD | 266 | 90.10 | 2.9E-2 |
| 204883_s_at | HUS1 | -0.5530751 | 0.57 | GOOD | 762 | 39.13 | 4.0E-3 |

TABLE D

Identification of non-homologous end-joining (NHEJ) genes whose expression associated with a prognostic value in DLBCL patients. NHEJ DNARSgenes.

| UNIQID | Name | Beta coefficient | HR | Prognostic value | Reference Level (ELRi) | Reference Level (ELRi) Percentage in patients' cohort | Benjamini Hochberg corrected p value |
|---|---|---|---|---|---|---|---|
| 222238_s_at | POLM | 0.784056395 | 2.19 | BAD | 791 | 10.14 | 5.5E-4 |
| 218961_s_at | PNKP | 0.727294445 | 2.06 | BAD | 958 | 35.02 | 1.1E-4 |
| 209940_at | PARP3 | 0.680597758 | 1.97 | BAD | 510 | 28.74 | 2.4E-4 |
| 219418_at | NHEJ1 | 0.665769481 | 1.94 | BAD | 354 | 61.84 | 1.3E-3 |
| 210543_s_at | PRKDC | 0.629654053 | 1.87 | BAD | 983 | 38.89 | 5.1E-4 |
| 206554_x_at | SETMAR | 0.60837915 | 1.84 | BAD | 495 | 13.53 | 7.3E-3 |
| 210470_x_at | NONO | 0.542424905 | 1.72 | BAD | 2755 | 60.63 | 5.4E-3 |
| 208442_s_at | ATM | 0.499720498 | 1.65 | BAD | 357 | 55.31 | 7.6E-3 |
| 221049_s_at | POLL | 0.469809421 | 1.60 | BAD | 58 | 80.43 | 4.8E-2 |
| 201585_s_at | SFPQ | 0.460141348 | 1.58 | BAD | 1935 | 36.96 | 7.8E-3 |
| 200792_at | XRCC6 | 0.339750944 | 1.40 | BAD | 11903 | 37.68 | 4.5E-2 |
| 205072_s_at | XRCC4 | -0.361645632 | 0.69 | GOOD | 265 | 58.70 | 3.3E-2 |
| 232633_at | XRCC5 | -0.412236702 | 0.66 | GOOD | 142 | 62.56 | 1.6E-2 |
| 241379_at | APLF | -0.638821578 | 0.53 | GOOD | 149 | 27.29 | 4.2E-3 |
| 206235_at | LIG4 | -0.645131505 | 0.52 | GOOD | 174 | 82.13 | 9.0E-4 |

TABLE E

Identification of mismatch repair (MMR) genes whose expression associated with a prognostic value in DLBCL patients. MMR DNARS genes.

| UNIQID | Name | Beta coefficient | HR | Prognostic value | Reference Level (ELRi) | Reference Level (ELRi) Percentage in patients' cohort | Benjamini Hochberg corrected p value |
|---|---|---|---|---|---|---|---|
| 203422_at | POLD1 | 0.937222702 | 2.55 | BAD | 1732 | 12.08 | 5.1E-5 |
| 201115_at | POLD2 | 0.745750088 | 2.11 | BAD | 1006 | 64.49 | 5.3E-4 |
| 204603_at | EXO1 | 0.66162252 | 1.94 | BAD | 735 | 30.68 | 2.7E-4 |
| 204127_at | RFC3 | 0.642556456 | 1.90 | BAD | 1677 | 78.26 | 1.1E-2 |
| 202726_at | LIG1 | 0.624320566 | 1.87 | BAD | 1038 | 45.89 | 7.2E-4 |
| 204023_at | RFC4 | 0.542909362 | 1.72 | BAD | 2753 | 81.64 | 3.1E-2 |
| 221206_at | PMS2 | 0.541332725 | 1.72 | BAD | 985 | 35.02 | 2.1E-3 |

TABLE E-continued

Identification of mismatch repair (MMR) genes whose expression
associated with a prognostic value in DLBCL patients. MMR DNARS genes.

| UNIQID | Name | Beta coefficient | HR | Prognostic value | Reference Level (ELRi) | Reference Level (ELRi) Percentage in patients' cohort | Benjamini Hochberg corrected p value |
| --- | --- | --- | --- | --- | --- | --- | --- |
| 201529_s_at | RPA1 | 0.533510226 | 1.70 | BAD | 3026 | 34.54 | 2.3E−3 |
| 216026_s_at | POLE | 0.517879065 | 1.68 | BAD | 486 | 62.32 | 8.2E−3 |
| 202520_s_at | MLH1 | 0.469484016 | 1.60 | BAD | 3167 | 71.01 | 2.2E−2 |
| 201202_at | PCNA | −0.410969369 | 0.66 | GOOD | 9365 | 51.45 | 1.9E−2 |
| 202996_at | POLD4 | −0.415416729 | 0.66 | GOOD | 1701 | 58.94 | 1.5E−2 |
| 209507_at | RPA3 | −0.539724756 | 0.58 | GOOD | 5753 | 49.28 | 2.8E−3 |
| 205887_x_at | MSH3 | −0.571462588 | 0.56 | GOOD | 594 | 32.37 | 5.7E−3 |
| 1053_at | RFC2 | −0.598091457 | 0.55 | GOOD | 591 | 81.64 | 3.3E−3 |
| 202911_at | MSH6 | −0.606399031 | 0.54 | GOOD | 3593 | 54.59 | 7.0E−4 |

TABLE F

Identification of homologous recombination repair (HRR) genes whose
expression associated with a prognostic value in DLBCL patients. HRR DNARS genes.

| UNIQID | Name | Beta coefficient | HR | Prognostic value | Reference Level (ELRi) | Reference Level (ELRi) Percentage in patients' cohort | Benjamini Hochberg corrected p value |
| --- | --- | --- | --- | --- | --- | --- | --- |
| 225357_s_at | INO80 | 1.043217805 | 2.84 | BAD | 461 | 11.59 | 2.2E−5 |
| 203422_at | POLD1 | 0.937222702 | 2.55 | BAD | 1732 | 12.08 | 5.1E−5 |
| 37793_r_at | RAD51D | 0.801839469 | 2.23 | BAD | 307 | 14.73 | 1.2E−4 |
| 212275_s_at | SRCAP | 0.766767577 | 2.15 | BAD | 366 | 11.84 | 3.8E−4 |
| 201115_at | POLD2 | 0.745750088 | 2.11 | BAD | 1006 | 64.49 | 5.3E−4 |
| 1559716_at | INO80C | 0.710596522 | 2.03 | BAD | 221 | 46.38 | 2.5E−4 |
| 216299_s_at | XRCC3 | 0.710133464 | 2.03 | BAD | 342 | 17.39 | 3.3E−4 |
| 206092_x_at | RTEL1 | 0.695480723 | 2.00 | BAD | 251 | 47.58 | 2.5E−4 |
| 214299_at | TOP3A | 0.687124458 | 1.99 | BAD | 338 | 30.19 | 2.2E−4 |
| 204531_s_at | BRCA1 | 0.67706995 | 1.97 | BAD | 656 | 76.57 | 7.2E−3 |
| 227286_at | INO80E | 0.672685766 | 1.96 | BAD | 1030 | 38.65 | 2.6E−4 |
| 204603_at | EXO1 | 0.66162252 | 1.94 | BAD | 735 | 30.68 | 2.7E−4 |
| 224683_at | FBXO18 | 0.658901936 | 1.93 | BAD | 910 | 23.67 | 4.9E−4 |
| 65133_i_at | INO80B | 0.618076841 | 1.85 | BAD | 271 | 31.64 | 5.3E−4 |
| 214258_x_at | KAT5 | 0.614579831 | 1.85 | BAD | 1098 | 40.34 | 7.3E−4 |
| 202907_s_at | NBN | 0.587275512 | 1.80 | BAD | 3272 | 47.10 | 1.2E−3 |
| 205647_at | RAD52 | 0.567914651 | 1.76 | BAD | 187 | 52.42 | 2.3E−3 |
| 201756_at | RPA2 | 0.564240535 | 1.76 | BAD | 3573 | 23.19 | 2.2E−3 |
| 201529_s_at | RPA1 | 0.533510226 | 1.70 | BAD | 3026 | 34.54 | 2.4E−3 |
| 214727_at | BRCA2 | 0.51043993 | 1.66 | BAD | 324 | 10.14 | 2.7E−2 |
| 208442_s_at | ATM | 0.499720498 | 1.65 | BAD | 357 | 55.31 | 7.7E−3 |
| 228286_at | GEN1 | 0.497143979 | 1.64 | BAD | 2174 | 10.14 | 3.4E−2 |
| 1569868_s_at | EME2 | 0.494638013 | 1.64 | BAD | 372 | 47.10 | 5.8E−3 |
| 210416_s_at | CHEK2 | 0.493297869 | 1.64 | BAD | 624 | 29.71 | 5.5E−3 |
| 234464_s_at | EME1 | 0.481989713 | 1.62 | BAD | 687 | 70.53 | 2.0E−2 |
| 214816_x_at | C19orf40 | 0.480973838 | 1.62 | BAD | 220 | 65.22 | 1.7E−2 |
| 218463_s_at | MUS81 | 0.47906345 | 1.61 | BAD | 1353 | 49.52 | 7.1E−3 |
| 210410_s_at | MSH5 | 0.467628874 | 1.59 | BAD | 413 | 45.65 | 7.9E−3 |
| 210533_at | MSH4 | 0.463867816 | 1.59 | BAD | 89 | 16.67 | 2.1E−2 |
| 213561_at | MCM9 | 0.450697565 | 1.57 | BAD | 274 | 17.15 | 2.7E−2 |
| 205024_s_at | RAD51 | 0.44358785 | 1.56 | BAD | 1352 | 28.99 | 1.3E−2 |
| 1561122_a_at | RAD51B | 0.399553558 | 1.49 | BAD | 31 | 55.31 | 2.7E−2 |
| 208393_s_at | RAD50 | 0.364822252 | 1.44 | BAD | 1298 | 48.07 | 3.2E−2 |
| 208386_x_at | DMC1 | −0.339189946 | 0.71 | GOOD | 94 | 66.18 | 4.7E−2 |
| 202996_at | POLD4 | −0.415416729 | 0.66 | GOOD | 1701 | 58.94 | 1.5E−2 |
| 205395_s_at | MRE11A | −0.536078467 | 0.58 | GOOD | 784 | 74.15 | 3.2E−3 |
| 209507_at | RPA3 | −0.539724756 | 0.58 | GOOD | 5753 | 49.28 | 2.8E−3 |
| 227545_at | BARD1 | −0.643938312 | 0.52 | GOOD | 1637 | 15.70 | 2.3E−2 |
| 227931_at | INO80D | −0.727387673 | 0.48 | GOOD | 746 | 27.29 | 2.2E−3 |
| 207598_x_at | XRCC2 | −0.987804898 | 0.37 | GOOD | 492 | 10.39 | 7.3E−3 |

TABLE G

Set of predictive genes of combined DNA repair score.

| Gene ID Probeset | Gene Symbol | Beta coefficient | HR | Prognostic value | Reference Level (ELRi) | Reference Level (ELRi) Percentage in patients' cohort | Benjamini Hochberg corrected p value |
| --- | --- | --- | --- | --- | --- | --- | --- |
| 220255_at | FANCE | 0.993790143 | 2.70 | BAD | 198 | 89.86 | 1.0E−2 |
| 203422_at | POLD1 | 0.937222702 | 2.55 | BAD | 1732 | 12.08 | 5.1E−5 |
| 242804_at | POLN | 0.894544042 | 2.45 | BAD | 24 | 89.13 | 2.1E−2 |
| 218317_x_at | SLX1 | 0.834709914 | 2.30 | BAD | 859 | 67.39 | 4.6E−4 |
| 203564_at | FANCG | 0.826646149 | 2.29 | BAD | 1429 | 17.87 | 3.8E−5 |
| 222238_s_at | POLM | 0.784056395 | 2.19 | BAD | 791 | 10.14 | 5.5E−4 |
| 1552937_s_at | ATRIP | 0.7636288 | 2.15 | BAD | 759 | 10.14 | 8.4E−4 |
| 65591_at | WDR48 | 0.761522676 | 2.14 | BAD | 990 | 15.22 | 2.4E−4 |
| 201115_at | POLD2 | 0.745750088 | 2.11 | BAD | 1006 | 64.49 | 5.3E−4 |
| 218961_s_at | PNKP | 0.727294445 | 2.07 | BAD | 958 | 35.02 | 1.1E−4 |
| 214299_at | TOP3A | 0.687124458 | 1.99 | BAD | 338 | 30.19 | 2.1E−4 |
| 213008_at | FANCI | 0.681798555 | 1.98 | BAD | 509 | 89.61 | 4.9E−2 |
| 209940_at | PARP3 | 0.680597758 | 1.98 | BAD | 510 | 28.74 | 2.4E−4 |
| 203229_s_at | CLK2 | 0.673454119 | 1.96 | BAD | 2246 | 46.62 | 3.7E−4 |
| 219418_at | NHEJ1 | 0.665769481 | 1.95 | BAD | 354 | 61.84 | 2.7E−4 |
| 204603_at | EXO1 | 0.66162252 | 1.94 | BAD | 735 | 30.68 | 1.3E−3 |
| 204127_at | RFC3 | 0.642556456 | 1.90 | BAD | 1677 | 78.26 | 1.1E−2 |
| 210543_s_at | PRKDC | 0.629654053 | 1.88 | BAD | 983 | 38.89 | 4.9E−4 |
| 221800_s_at | C17orf70/FAAP100 | 0.626604357 | 1.87 | BAD | 578 | 41.55 | 7.2E−4 |
| 202726_at | LIG1 | 0.624320566 | 1.87 | BAD | 1038 | 45.89 | 5.1E−4 |
| 235215_at | ERCC4 | 0.619519753 | 1.86 | BAD | 617 | 12.32 | 5.0E−3 |
| 206554_x_at | SETMAR | 0.60837915 | 1.84 | BAD | 495 | 13.53 | 7.3E−3 |
| 223545_at | FANCD2 | 0.593972707 | 1.81 | BAD | 322 | 54.35 | 6.1E−3 |
| 203678_at | FAN1 | 0.592337616 | 1.81 | BAD | 400 | 69.57 | 1.7E−3 |
| 203805_s_at | FANCA | 0.571168788 | 1.77 | BAD | 1250 | 29.47 | 1.4E−3 |
| 201756_at | RPA2 | 0.564240535 | 1.76 | BAD | 3573 | 23.19 | 2.2E−3 |
| 205189_s_at | FANCC | 0.559293676 | 1.75 | BAD | 473 | 24.88 | 2.1E−3 |
| 204023_at | RFC4 | 0.542909362 | 1.72 | BAD | 2753 | 81.64 | 5.4E−3 |
| 210470_x_at | NONO | 0.542424905 | 1.72 | BAD | 2755 | 60.63 | 2.1E−3 |
| 221206_at | PMS2 | 0.541332725 | 1.72 | BAD | 985 | 35.02 | 3.1E−2 |
| 201529_s_at | RPA1 | 0.533510226 | 1.70 | BAD | 3026 | 34.54 | 2.3E−3 |
| 205394_at | CHEK1 | 0.528159908 | 1.70 | BAD | 1541 | 13.53 | 1.6E−2 |
| 216026_s_at | POLE | 0.517879065 | 1.68 | BAD | 486 | 62.32 | 8.2E−3 |
| 222713_s_at | FANCF | 0.516794711 | 1.68 | BAD | 669 | 17.15 | 1.3E−2 |
| 214727_at | BRCA2 | 0.51043993 | 1.67 | BAD | 324 | 10.14 | 2.7E−2 |
| 208442_s_at | ATM | 0.499720498 | 1.65 | BAD | 357 | 55.31 | 7.6E−3 |
| 218428_s_at | REV1 | 0.487390595 | 1.63 | BAD | 1095 | 62.08 | 1.1E−2 |
| 234464_s_at | EME1 | 0.481989713 | 1.62 | BAD | 687 | 70.53 | 1.7E−2 |
| 214816_x_at | C19orf40/FAAP24 | 0.480973838 | 1.62 | BAD | 220 | 65.22 | 2.0E−2 |
| 218463_s_at | MUS81 | 0.47906345 | 1.61 | BAD | 1353 | 49.52 | 7.1E−3 |
| 221049_s_at | POLL | 0.469809421 | 1.60 | BAD | 58 | 80.43 | 2.2E−2 |
| 202520_s_at | MLH1 | 0.469484016 | 1.60 | BAD | 3167 | 71.01 | 4.8E−2 |
| 201585_s_at | SFPQ | 0.460141348 | 1.58 | BAD | 1935 | 36.96 | 7.8E−3 |
| 205024_s_at | RAD51 | 0.44358785 | 1.56 | BAD | 1352 | 28.99 | 1.3E−2 |
| 233852_at | POLH | 0.430217571 | 1.54 | BAD | 642 | 31.16 | 1.4E−2 |
| 219317_at | POLI | 0.398668422 | 1.49 | BAD | 424 | 54.59 | 2.4E−2 |
| 200792_at | XRCC6 | 0.339750944 | 1.40 | BAD | 11903 | 37.68 | 4.5E−2 |
| 205072_s_at | XRCC4 | −0.361645632 | 0.70 | GOOD | 265 | 58.70 | 3.3E−2 |
| 201202_at | PCNA | −0.410969369 | 0.66 | GOOD | 9365 | 51.45 | 1.9E−2 |
| 232633_at | XRCC5 | −0.412236702 | 0.66 | GOOD | 142 | 62.56 | 1.5E−2 |
| 202996_at | POLD4 | −0.415416729 | 0.66 | GOOD | 1701 | 58.94 | 1.6E−2 |
| 209507_at | RPA3 | −0.539724756 | 0.58 | GOOD | 5753 | 49.28 | 2.8E−3 |
| 1557217_a_at | FANCB | −0.561972725 | 0.57 | GOOD | 24 | 77.29 | 2.4E−3 |
| 205887_x_at | MSH3 | −0.571462588 | 0.56 | GOOD | 594 | 32.37 | 5.7E−3 |
| 1053_at | RFC2 | −0.598091457 | 0.55 | GOOD | 591 | 81.64 | 3.3E−3 |
| 202911_at | MSH6 | −0.606399031 | 0.55 | GOOD | 3593 | 54.59 | 7.0E−4 |
| 241379_at | APLF | −0.638821578 | 0.53 | GOOD | 149 | 27.29 | 4.2E−3 |
| 206235_at | LIG4 | −0.645131505 | 0.52 | GOOD | 174 | 82.13 | 9.0E−4 |
| 202412_s_at | USP1 | −0.661144729 | 0.52 | GOOD | 1146 | 54.83 | 4.5E−4 |

Methods for Predicting Response

The present invention relates to a method of testing whether a patient suffering from diffuse large B-cell lymphoma will respond or not to a DNA repair pathway inhibitor comprising:
i) determining the expression level (ELi) of several genes $G_1$-$G_n$ selected from table A in a biological sample obtained from said patient
ii) comparing the expression level (ELi) determined at step i) with a predetermined reference level (ELRi)
iii) calculating the DNA repair score trough the following formula $$DNARS = \sum_{i=1}^{n} \beta i \times Ci$$

wherein $\beta i$ represent the regression $\beta$ coefficient reference value for the gene $G_i$ and Ci=1 if the expression of the gene $G_i$ (ELi) is higher than the predetermined reference level (ELRi) or Ci=−1 if the expression of the gene (ELi) is lower than or equal to the predetermined reference level (ELRi)
iv) comparing the score DNARS determined at step iii) with a predetermined reference value $DNARS_R$
v) and concluding that the patient will respond to the treatment when the DNARS score is higher than the predetermined reference value $DNARS_R$ or concluding that the patient will not respond to the treatment when the DNARS score is lower than the predetermined reference value $DNARS_R$.

In some embodiments, the levels of the 126 genes of Tables A, B, C, D, E, F and G are determined.

In some embodiments, the present invention relates to a method of testing whether a patient suffering of diffuse large B-cell lymphoma will respond or not to a FANC inhibitor according to the invention wherein the step i) comprises determining the expression level (ELi) of 33 genes from Table A.

In some embodiments, the levels of at least 33 genes from Table A are determined wherein said genes are: FANCE, POLN, SLX1, FANCG, WDR48, ATRIP, TOP3A, FANCI, CLK2, C17orf70/FAAP100, ERCC4, FANCD2, FAN1, FANCA, RPA2, FANCC, PMS2, RPA1, CHEK1, FANCF, BRCA2, ATM, REV1, EME1, C19orf40/FAAP24, MUS81, MLH1, RAD51, POLH, POLI, RPA3, FANCB, USP1.

In some embodiments, the levels of the 33 genes of Table A are determined.

In some embodiments, the present invention relates to a method of testing whether a patient suffering of diffuse large B-cell lymphoma will respond or not to a NER inhibitor according to the invention wherein the step i) comprises determining the expression level (ELi) of 29 genes from Table B.

In some embodiments, the levels of at least 29 genes from Table B are determined wherein said genes are: POLD1, LIG3, MMS19, ERCC2, CUL4A, UVSSA, GTF2H4/TFIIH4, LIG1, ERCC8, ERCC4, RAD23A, XAB2, RPA2, XPA, RPA1, POLE, RAD23B, DDB1, ERCC3, PCNA, MNAT1, GTF2H1/TFIIH1, GTF2H5/TFIIH5, XPC, CCNH, RBX1, RPA3, CETN2, ERCC5.

In some embodiments, the levels of the 29 genes of Table B are determined.

In some embodiments, the present invention relates to a method of testing whether a patient suffering of diffuse large B-cell lymphoma will respond or not to a BER inhibitor according to the invention wherein the step i) comprises determining the expression level (ELi) of 23 genes from Table C.

In some embodiments, the levels of at least 23 genes from Table C are determined wherein said genes are: POLD1, LIG3, NTHL1, POLD2, APTX, MUTYH, PNKP, APEX2, PARP2, NEIL2, LIG1, POLE, NEIL3, POLL, UNG, XRCC1, POLH, APEX1, PCNA, POLD4, NEIL1, OGG1, HUS1.

In some embodiments, the levels of the 23 genes of Table C are determined.

In some embodiments, the present invention relates to a method of testing whether a patient suffering of diffuse large B-cell lymphoma will respond or not to a NHEJ inhibitor according to the invention wherein the step i) comprises determining the expression level (ELi) of 15 genes from Table D.

In some embodiments, the levels of at least 15 genes from Table D are determined wherein said genes are: POLM, PNKP, PARP3, NHEJ1, PRKDC, SETMAR, NONO, ATM, POLL, SFPQ, XRCC6, XRCC4, XRCC5, APLF, LIG4.

In some embodiments, the levels of the 15 genes of Table D are determined.

In some embodiments, the present invention relates to a method of testing whether a patient suffering of diffuse large B-cell lymphoma will respond or not to a MMR inhibitor according to the invention wherein the step i) comprises determining the expression level (ELi) of 16 genes from Table E.

In some embodiments, the levels of at least 16 genes from Table E are determined wherein said genes are: POLD1, POLD2, EXO1, RFC3, LIG1, RFC4, PMS2, RPA1, POLE, MLH1, PCNA, POLD4, RPA3, MSH3, RFC2, MSH6.

In some embodiments, the levels of the 16 genes of Table E are determined.

In some embodiments, the present invention relates to a method of testing whether a patient suffering of diffuse large B-cell lymphoma will respond or not to a HRR inhibitor according to the invention wherein the step i) comprises determining the expression level (ELi) of 40 genes from Table F.

In some embodiments, the levels of at least 40 genes from Table F are determined wherein said genes are: INO80, POLD1, RAD51D, SRCAP, POLD2, INO80C, XRCC3, RTEL1, TOP3A, BRCA1, INO80E, EXO1, FBXO18, INO80B, KATS, NBN, RAD52, RPA2, RPA1, BRCA2, ATM, GENT, EME2, CHEK2, EME1, C19orf40, MUS81, MSH5, MSH4, MCM9, RAD51, RAD51B, RAD50, DMC1, POLD4, MRE11A, RPA3, BARD1, INO80D, XRCC2.

In some embodiments, the levels of the 40 genes of Table F are determined.

In some embodiments, the present invention relates to a method of testing whether a patient suffering of diffuse large B-cell lymphoma will respond or not to a DNA repair pathway inhibitor targeting several DNA repair pathways or to at least 2 DNA repair pathway inhibitors selected from FANC, NHEJ, or MMR DNA repair pathway inhibitor according to the invention wherein the step i) comprises determining the expression level (ELi) of 59 genes from Table G.

In some embodiments, the levels of at least 59 genes from Table F are determined wherein said genes are: FANCE, POLD1, POLN, SLX1, FANCG, POLM, ATRIP, WDR48, POLD2, PNKP, TOP3A, FANCI, PARP3, CLK2, NHEJ1, EXO1, RFC3, PRKDC, C17orf70/FAAP100, LIG1, ERCC4, SETMAR, FANCD2, FAN1, FANCA, RPA2, FANCC, RFC4, NONO, PMS2, RPA1, CHEK1, POLE, FANCF, BRCA2, ATM, REV1, EME1, C19orf40/FAAP24, MUS81, POLL, MLH1, SFPQ, RAD51, POLH, POLI, XRCC6, XRCC4, PCNA, XRCC5, POLD4, RPA3, FANCB, MSH3, RFC2, MSH6, APLF, LIG4, USP1.

In some embodiments, the levels of the 59 genes of Table F are determined.

In a further aspect, the present invention relates to a method of testing whether a patient suffering of diffuse large B-cell lymphoma will respond or not to a BER inhibitor comprising the steps of:
  i) performing the method according to the invention,
  ii) and concluding that the patient will respond to the BER inhibitor when the BER DNARS score is higher than the predetermined reference value BER $DNARS_R$ and the HRR DNARS score is lower than the predetermined reference value HRR $DNARS_R$, or concluding that the patient will not respond to the BER inhibitor when the BER DNARS score is lower than the predetermined reference value BER $DNARS_R$ or the HRR DNARS score is higher than the predetermined reference value HRR $DNARS_R$.

In a particular embodiment, the BER inhibitor is a PARP inhibitor.

Determination of the expression level of the genes can be performed by a variety of techniques. Generally, the expression level as determined is a relative expression level. More preferably, the determination comprises contacting the biological sample with selective reagents such as probes, primers or ligands, and thereby detecting the presence, or measuring the amount, of polypeptide or nucleic acids of interest originally in the biological sample. Contacting may be performed in any suitable device, such as a plate, microtiter dish, test tube, well, glass, column, and so forth. In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the biological sample.

In a preferred embodiment, the expression level may be determined by determining the quantity of mRNA.

Methods for determining the quantity of mRNA are well known in the art. For example the nucleic acid contained in the biological sample is first extracted according to standard methods, for example using lytic enzymes or chemical solutions or extracted by nucleic-acid-binding resins following the manufacturer's instructions. The extracted mRNA is then detected by hybridization (e. g., Northern blot analysis) and/or amplification (e.g., RT-PCR). Preferably quantitative or semi-quantitative RT-PCR is preferred. Real-time quantitative or semi-quantitative RT-PCR is particularly advantageous.

Other methods of amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e. g. avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In a particular embodiment, the methods of the invention comprise the steps of providing total RNAs extracted from a biological samples and subjecting the RNAs to amplification and hybridization to specific probes, more particularly by means of a quantitative or semi-quantitative RT-PCR.

In another preferred embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a biological sample from a test patient, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210)

In this context, the invention further provides a DNA chip comprising a solid support which carries nucleic acids that are specific to the genes listed in Tables A, B, C, D, E, F, and G.

Predetermined reference values ELRi or $DNARS_R$ used for comparison may consist of "cut-off" values.

For example; each reference ("cut-off") value ELRi for each gene may be determined by carrying out a method comprising the steps of:

a) providing a collection of samples from patients suffering from diffuse large B-cell lymphoma;

b) determining the expression level of the relevant gene for each sample contained in the collection provided at step a);

c) ranking the samples according to said expression level d) classifying said samples in pairs of subsets of increasing, respectively decreasing, number of members ranked according to their expression level, e) providing, for each sample provided at step a), information relating to the actual clinical outcome for the corresponding cancer patient (i.e. the duration of the disease-free survival (DFS), or the event free survival (EFS) or the overall survival (OS) or both);

f) for each pair of subsets of tumour tissue samples, obtaining a Kaplan Meier percentage of survival curve;

g) for each pair of subsets of tumour tissue samples calculating the statistical significance (p value) between both subsets h) selecting as reference value ELR for the expression level, the value of expression level for which the p value is the smallest.

For example the expression level of a gene Gi has been assessed for 100 samples of 100 patients. The 100 samples are ranked according to the expression level of gene Gi. Sample 1 has the highest expression level and sample 100 has the lowest expression level. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding cancer patient, Kaplan Meier curves are prepared for each of the 99 groups of two subsets. Also for each of the 99 groups, the p value between both subsets was calculated. The reference value ELRi is then selected such as the discrimination based on the criterion of the minimum p value is the strongest. In other terms, the expression level corresponding to the boundary between both subsets for which the p value is minimum is considered as the reference value. It should be noted that according to the experiments made by the inventors, the reference value ELRi is not necessarily the median value of expression levels.

The man skilled in the art also understands that the same technique of assessment of the $DNARS_R$ could be used for obtaining the reference value and thereafter for assessment of the response to the combination treatment of the present invention. However in one embodiment, the reference value $DNARS_R$ is the median value of DNARS.

In one embodiment, the reference value ELRi for the gene Gi is described in tables A, B, C, D, E, F, and G (right column).

The regression β coefficient reference values may be easily determined by the skilled man in the art for each gene Gi using a Cox model. The Cox model is based on a modeling approach to the analysis of survival data. The purpose of the model is to simultaneously explore the effects of several variables on survival. The Cox model is a well-recognised statistical technique for analysing survival data. When it is used to analyse the survival of patients in a clinical trial, the model allows us to isolate the effects of treatment from the effects of other variables. The logrank test cannot be used to explore (and adjust for) the effects of several variables, such as age and disease duration, known to affect survival. Adjustment for variables that are known to affect survival may improve the precision with which we can estimate the treatment effect. The regression method introduced by Cox is used to investigate several variables at a time. It is also known as proportional hazards regression analysis. Briefly, the procedure models or regresses the survival times (or more specifically, the so-called hazard function) on the explanatory variables. The hazard function is the probability that an individual will experience an event (for example, death) within a small time interval, given that the individual has survived up to the beginning of the interval. It can therefore be interpreted as the risk of dying at time t. The quantity h0 (t) is the baseline or underlying hazard function and corresponds to the probability of dying (or reaching an event) when all the explanatory variables are zero. The baseline hazard function is analogous to the intercept in ordinary regression (since exp0=1). The regression coefficient β gives the proportional change that can be expected in the hazard, related to changes in the explanatory variables. The coefficient β is estimated by a statistical method called maximum likelihood. In survival analysis, the hazard ratio (HR) (Hazard Ratio=exp(β)) is the ratio of the hazard rates corresponding to the conditions described by two sets of explanatory variables. For example, in a drug study, the treated population may die at twice the rate per unit time as the control population. The hazard ratio would be 2, indicating higher hazard of death from the treatment.

In one embodiment, the regression β coefficient reference values are described in Tables A, B, C, D, E, F, and G.

Typically, the reference value FANC $DNARS_R$ is −5.24 for determining whether a patient suffering of diffuse large B-cell lymphoma will respond to a FANC DNA repair pathway inhibitor and for predicting the survival time of patient suffering of diffuse large B-cell lymphoma.

Typically, the reference value NER $DNARS_R$ is −7.78 for determining whether a patient suffering of diffuse large B-cell lymphoma will respond to a NER DNA repair pathway inhibitor and for predicting the survival time of patient suffering of diffuse large B-cell lymphoma.

Typically, the reference value BER $DNARS_R$ is −5.10 for determining whether a patient suffering of diffuse large B-cell lymphoma will respond to a BER DNA repair pathway inhibitor and for predicting the survival time of patient suffering of diffuse large B-cell lymphoma.

Typically, the reference value NHEJ $DNARS_R$ is −5.27 for determining whether a patient suffering of diffuse large B-cell lymphoma will respond to a NHEJ DNA repair pathway inhibitor and for predicting the survival time of patient suffering of diffuse large B-cell lymphoma.

Typically, the reference value MMR $DNARS_R$ is −3.07 for determining whether a patient suffering of diffuse large B-cell lymphoma will respond to a MMR DNA repair pathway inhibitor and for predicting the survival time of patient suffering of diffuse large B-cell lymphoma.

Typically, the reference value HRR $DNARS_R$ is −8.67 for determining whether a patient suffering of diffuse large B-cell lymphoma will respond to a HRR DNA repair pathway inhibitor and for predicting the survival time of patient suffering of diffuse large B-cell lymphoma.

Typically, the reference values of the combined DNA Repair score $DNARS_R$ are −19.523 and −9.822 for determining whether a patient suffering of diffuse large B-cell lymphoma will respond to a DNA repair pathway inhibitor targeting several DNA repair pathways or to at least 2 DNA repair pathway inhibitors selected from FANC, NHEJ, or MMR DNA repair pathway inhibitor and for predicting the survival time of patient suffering of diffuse large B-cell lymphoma.

The invention also relates to a kit for performing the methods as above described, wherein said kit comprises means for measuring the expression level of the genes listed in Tables A, B, C, D, E, F and G. Typically the kit may include a primer, a set of primers, a probe, a set of probes as above described. In a particular embodiment, the probe or set of probes are labelled as above described. The kit may also contain other suitably packaged reagents and materials needed for the particular detection protocol, including solid-phase matrices, if applicable, and standards.

In a particular embodiment, the score may be generated by a computer program.

Methods of Treatment

The method of the invention allows to define a subgroup of patients who will be responsive ("responder") or not ("non responder") to the treatment with a DNA repair pathway inhibitor.

In a particular embodiment, the method of the invention allows to define a subgroup of patients who will be responsive ("responder") or not ("non responder") to the treatment with a FANC, NER, BER, NHEJ, MMR or HRR DNA repair pathway inhibitor.

In a particular embodiment, the method of the invention allows to define a subgroup of patients who will be responsive ("responder") or not ("non responder") to the treatment with a DNA repair pathway inhibitor targeting several DNA repair pathways or to the treatment with at least 2 DNA repair pathway inhibitors selected from FANC, NHEJ, or MMR DNA repair pathway inhibitor.

A further object of the invention relates to a method for the treatment of diffuse large B-cell lymphoma in a patient in need thereof.

In the context of the invention, the term "treating" or "treatment", as used herein, means reversing, alleviating, inhibiting the progress of, or preventing the disorder or condition to which such term applies, or one or more symptoms of such disorder or condition.

In a particular embodiment, the method comprises the following steps:

a) testing whether the patient will respond or not to the DNA repair pathway by performing the method according to the invention b) administering the DNA repair pathway inhibitor when the DNARS score is higher than the reference value $DNARS_R$ (i.e. the patient will respond to the DNA repair pathway inhibitor).

In some embodiments, the present invention relates to a method for the treatment of diffuse large B-cell lymphoma in a patient in need thereof comprising the steps of:

a) testing whether the patient will respond or not to a DNA repair pathway inhibitor by performing the method according to the invention, b) administering the FANC inhibitor, if said patient has a score higher than the reference value FANC $DNARS_R$, administering the NER inhibitor, if said patient has a score higher than the reference value NER $DNARS_R$, administering the BER inhibitor, if said patient has a score higher than the reference value BER $DNARS_R$, administering the NHEJ inhibitor, if said patient has a score higher than the reference value NHEJ $DNARS_R$, administering the MMR inhibitor, if said patient has a score higher than the reference value MMR $DNARS_R$, administering the HRR inhibitor, if said patient has a score higher than the reference value HRR $DNARS_R$, and administering the DNA repair pathway inhibitor targeting several DNA repair pathways or at least 2 DNA repair pathway inhibitors selected from FANC, NHEJ, or MMR DNA repair pathway inhibitor, if said patient has as score higher than the reference value of the combined DNA repair score $DNARS_R$.

In a further aspect, the present invention relates to a method for the treatment of diffuse large B-cell lymphoma in a patient in need thereof comprising the steps of:

a) testing whether the patient will respond or not to a DNA repair pathway inhibitor by performing the method according to the invention, b) administering the BER inhibitor, if said patient has a score higher than the reference value BER $DNARS_R$, and a score lower than the reference value HRR $DNARS_R$.

In a particular embodiment, the BER inhibitor is a PARP inhibitor.

A further object of the invention relates to a DNA repair pathway inhibitor for use in the treatment of diffuse large B-cell lymphoma in a patient in need thereof, wherein the patient was being classified as responder by the method as above described.

In some embodiments, the DNA repair pathway inhibitor is selected from FANC, NER, BER, NHEJ, MMR, HRR DNA repair pathway inhibitors, or DNA repair pathway inhibitor targeting several DNA repair pathways.

In a particular embodiment, the invention relates to a BER DNA repair pathway inhibitors such as PARP inhibitor for use in the treatment of diffuse large B-cell lymphoma in a patient in need thereof, wherein the patient has a BER DNARS score higher than the reference value BER $DNARS_R$, and a HRR DNARS score lower than the reference value HRR $DNARS_R$.

A further object of the invention relates to a combination treatment consisting of DNA repair pathway inhibitor selected from FANC, NER, BER, NHEJ, MMR and HRR DNA repair pathway inhibitors and conventional diffuse large B-cell lymphoma treatment such as anthracycline-based chemotherapy regimens such as a combination of cyclophosphamide, doxorubicin, vincristine, and prednisone (CHOP) and Rituximab-CHOP chemotherapy regimens (R-CHOP) for use in the treatment of diffuse large B-cell lymphoma in a patient in need thereof, wherein the patient was being classified as responder by the method as above described.

In some embodiments, the FANC, NER, BER, NHEJ, MMR and HRR DNA repair pathway inhibitors are selected from the compounds described in TABLE H.

TABLE H

Small molecule inhibitors of DNA damage response factors in preclinical or clinical development for cancer therapy.

| Target | Inhibitor | Mono- or combination therapy/clinical study stage | Clinical trial identifier/reference |
|---|---|---|---|
| ATM (useful taget to prevent repair of DSBs in cancer cells) | KU-55933 | IR, etoposide, doxorubicin, camptothecin, in preclinical testing | (45, 46) |
| | KU-60019 | IR in preclinical testing using glioma cells | (47) |
| ATR (useful taget to prevent repair of DSBs in cancer cells) | NU-6027 | Hydroxyurea, cisplatin, temozolomide, rucaparib in preclinical testing | (48) |
| | VE-821 | Cisplatin in breast and ovarian cell lines IR, gemcitabine in pancreatic cancer cells in preclinical testing | (49-51) |
| | ETP-46464 | Single agent in p53-deficient cancer cells in preclinical testing | (52) |
| DNA-PKcs (essential kinase for NHEJ of DSBs) | NU-7441 | IR, etoposide in preclinical testing of cancer cell lines and tumour xenografts | (53, 54) |
| | NU-7026 | IR and combined with AG14361 (PARPi) in preclinical testing Anthracyclines, mitoxantrone, etoposide in preclinical testing using leukaemia cells | (55, 56) |
| DNA-PKcs/PI3K | KU-60648 | Etoposide, doxorubicin in preclinical testing | (57) |
| NA-PKcs/mTOR | CC-115 | Single agent in Phase I safety and tolerability study (recruiting) | NCT01353625 |
| ATM (useful taget to prevent repair of DSBs in cancer cells) | CP466722 | In preclinical testing | (58) |
| CHK1/(CHK2) (useful taget to prevent repair of DSBs in cancer cells) | UCN-01 | Single agent in Phase II for relapsed T-cell lymphoma (completed) Single agent in Phase II for metastatic melanoma (completed) Five-fluorouracil in Phase II for metastatic pancreatic cancer (completed) Topotecan in Phase II for various forms of ovarian cancer (completed) Topotecan in Phase II for small cell lung cancer (completed) Olaparib in pre-clinical testing for multiple mammary tumour types | NCT00082017 NCT00072189 NCT00045747 NCT00072267 NCT00098956 (59) |
| | GDC-0425 | Single agent or with gemcitabine in Phase I dose-escalation study (recruiting) | NCT01359696 |
| | MK-8776 | Single agent or with gemcitabine in Phase I dose-escalation study (completed) | NCT00779584 |
| | LY-2606368 | Single agent in Phase I study in patients with advanced cancer (recruiting) | NCT01115790 |
| WEE1 (DNA damage repair regulation - DNA damage checkpoint) | MK-1775 | Carboplatin in Phase II for epithelial ovarian cancer | NCT01164995 |
| CDC25 (DNA damage checkpoint) | IRC-083864 | Single agent in preclinical testing using pancreatic and prostate cancer cells | (60) |
| MRE11 (DSBs repair) | mirin | Single agent or with olaparib (PARPi) in preclinical testing using BRCA2-deficient cells | (61) |
| RPA (HR pathway) | MC113E | Single agent or with cisplatin in preclinical testing | (62) |
| RAD51 (HR pathway) | B02 | IR, mitomycin C, cisplatin in preclinical testing | (63) |
| | RI-1 | Mitomyin C in preclinical testing | (64) |
| MGMT inh (MMR pathway) | Lomeguatrib | Phase I-Phase II | (65, 66) |
| MGMT inh (MMR pathway) | O6-benzylguanine | Phase II | (65) |
| APE inh (BER pathway) | TRC102 | Phase I | (65) |
| PARP inh (BER, alt NHEJ pathway) | Iniparib | Phase II-III | (65) |
| PARP inh (BER, alt NHEJ pathway) | Veliparib | Phase I-II | (65) |
| PARP inh (BER, alt NHEJ pathway) | Olaparib | Phase I-II | (65) |
| PARP inh (BER, alt NHEJ pathway) | CEP-8933 | Phase I | (65) |
| PARP inh (BER, alt NHEJ pathway) | INO-1001 | Phase I | (65) |

TABLE H-continued

Small molecule inhibitors of DNA damage response factors in
preclinical or clinical development for cancer therapy.

| Target | Inhibitor | Mono- or combination therapy/clinical study stage | Clinical trial identifier/reference |
|---|---|---|---|
| PARP inh (BER, alt NHEJ pathway) | AG014699 | Phase I | (65) |
| PARP inh (BER, alt NHEJ pathway) | GPI21016 | Phase I | (65) |
| PARP inh (BER, alt NHEJ pathway) | MK4827 | Phase I | (65) |

The invention will be further illustrated by the following figures and examples. However, these examples and figures should not be interpreted in any way as limiting the scope of the present invention.

FIGURES

FIG. 1: Prognostic Value of DNA Repair Scores in DLBCL Patients

Patients of the R-CHOP cohort (n=233) were ranked according to increasing FANC (A), NER (B), HRR (C), BER (D), NHEJ (E) and MMR (F) scores and a maximum difference in OS was obtained using Maxstat R function. The prognostic value of FANC (A), NER (B), HRR (C), BER (D), NHEJ (E) and MMR (F) scores was validated on an independent cohort of 181 patients treated with CHOP regimen.

Figure 2:
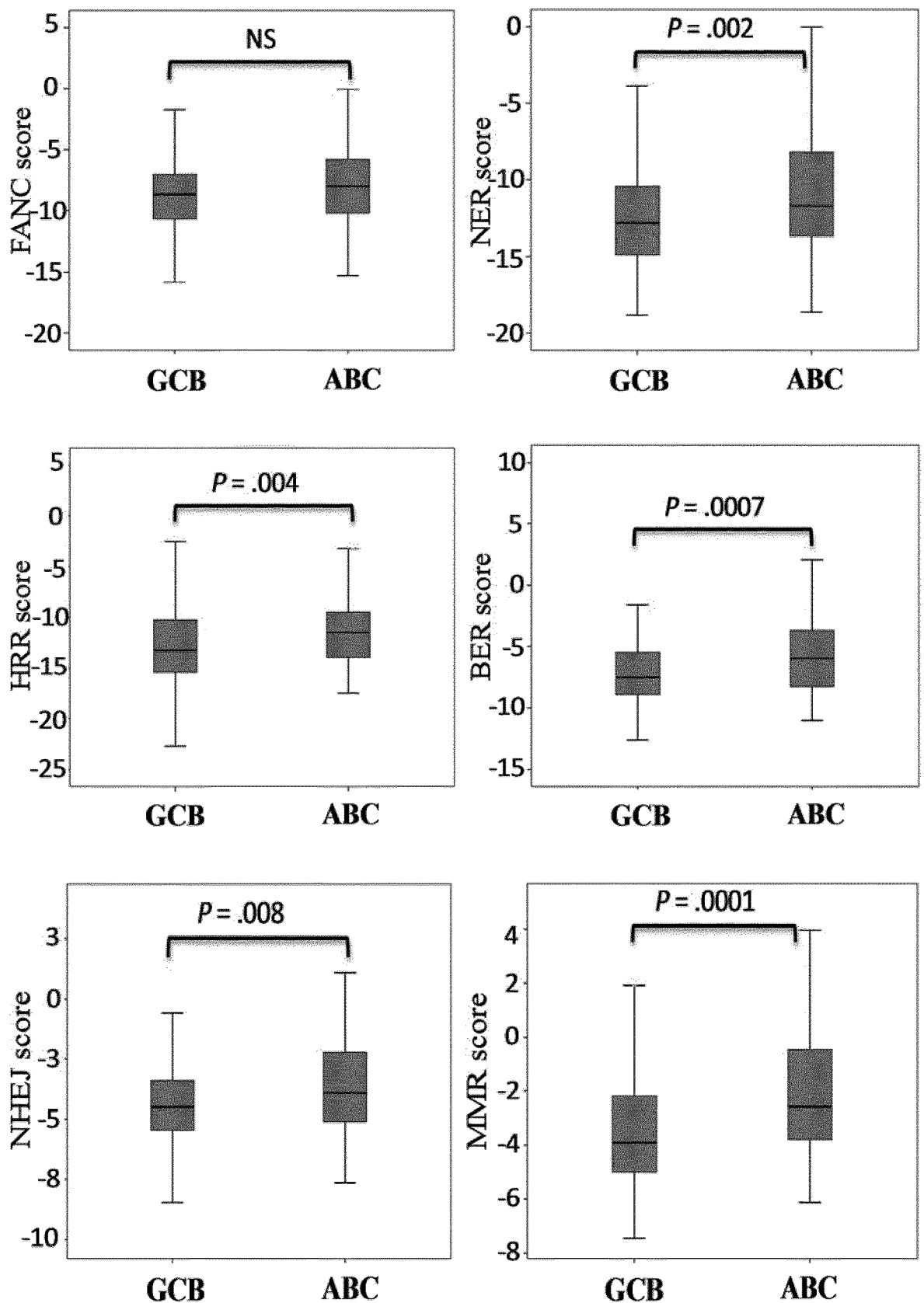

FIG. 2: FANC, NER, HRR, BER, NHEJ, and MMR Scores in ABC and GCB Molecular Subgroups FANC, NER, HRR, BER, NHEJ and MMR scores were investigated in activated B-cell like (ABC) and germinal center B-cell like (GCB) molecular subgroups of DLBCL patients (R-CHOP cohort, n=200).

Figure 3A:
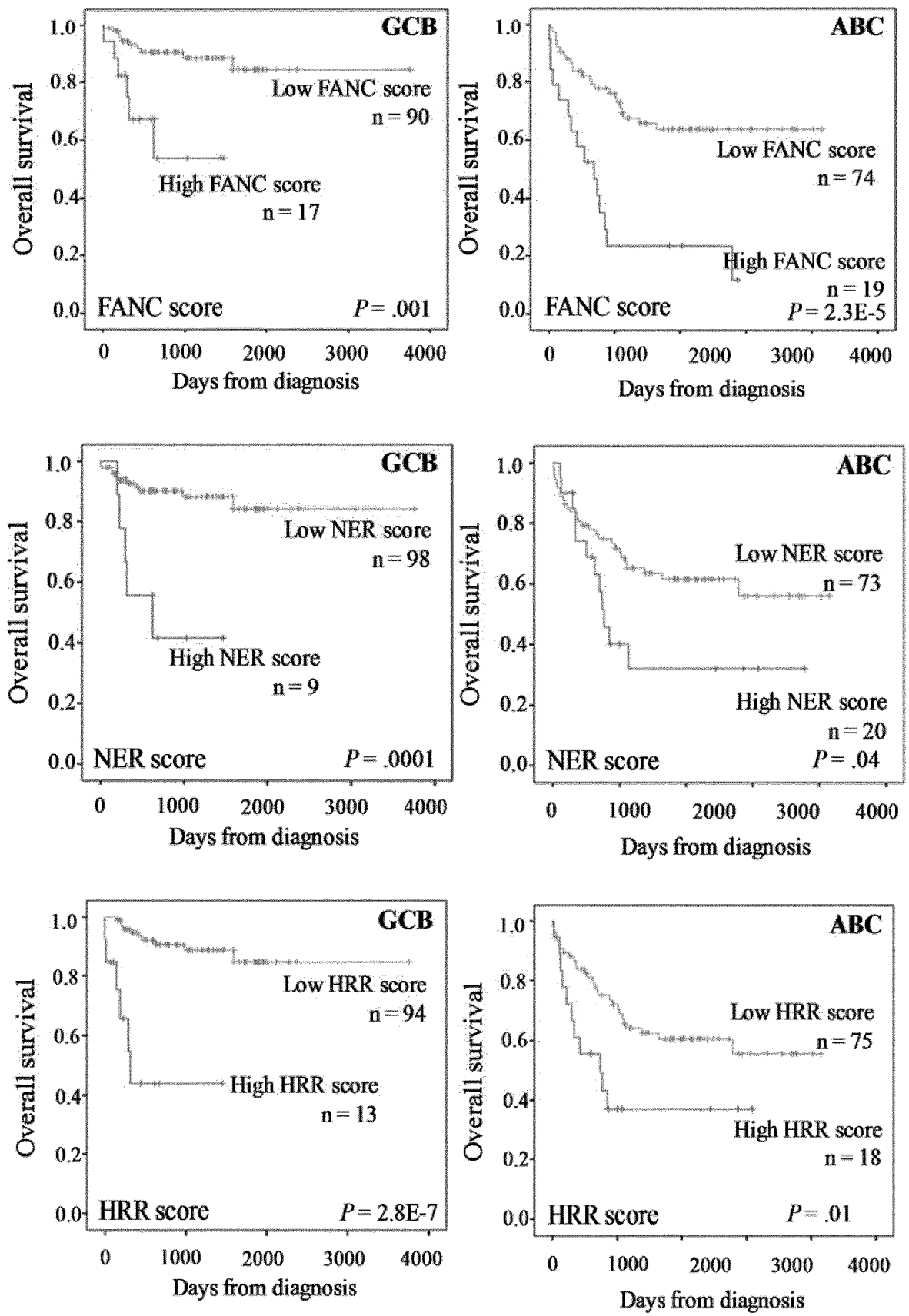
Figure 3B:
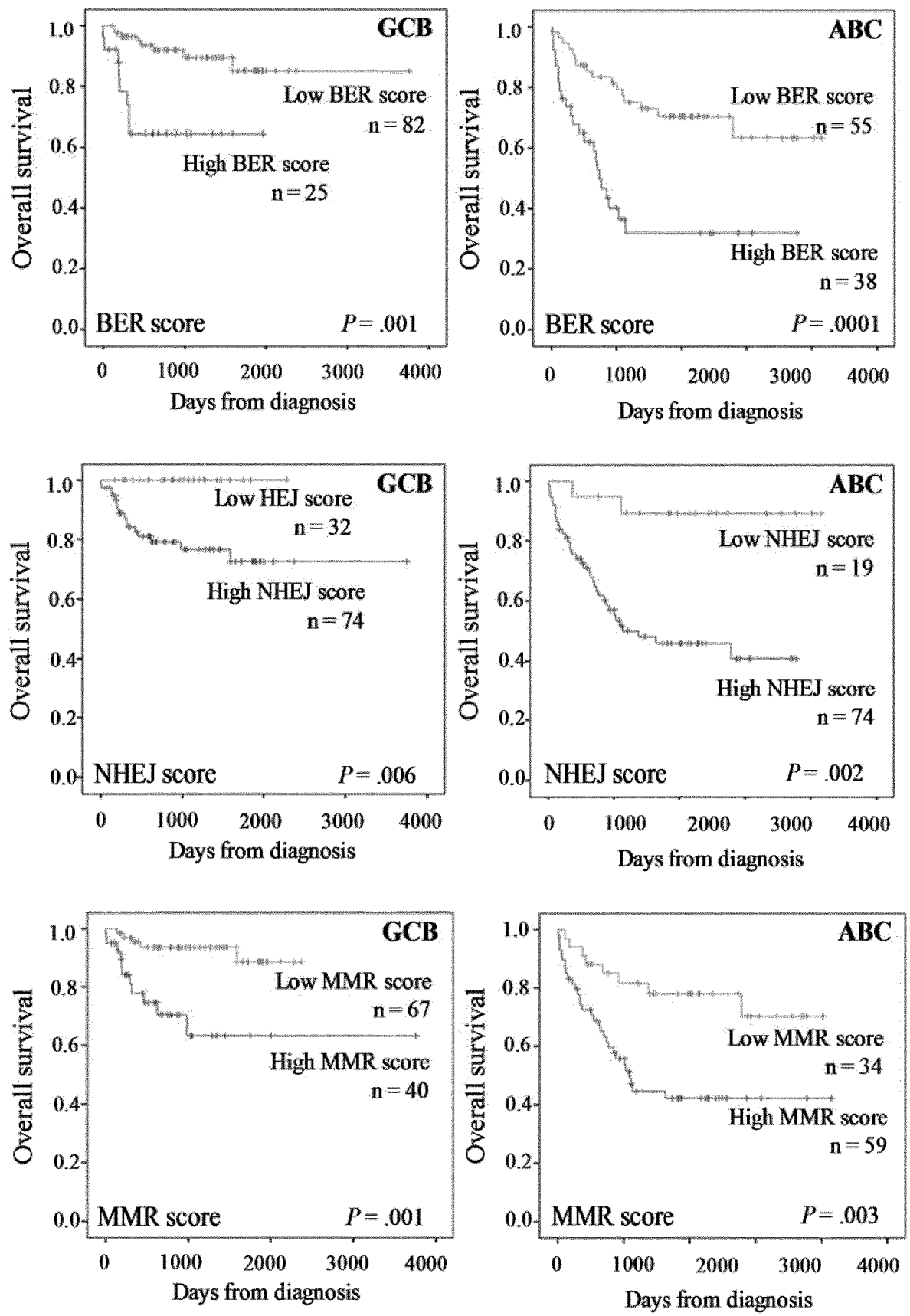

FIG. 3: Prognostic Prediction Applying FANC, NER, HRR, BER, NHEJ and MMR Scores in ABC/GCB Subgroups of DLBCL Patients The prognostic value of FANC, NER, and HRR scores (A), BER, NHEJ and MMR scores (B) was tested in DLBCL patients of GCB molecular subgroup (n=107) and ABC molecular subgroup (n=93).

Figure 4:
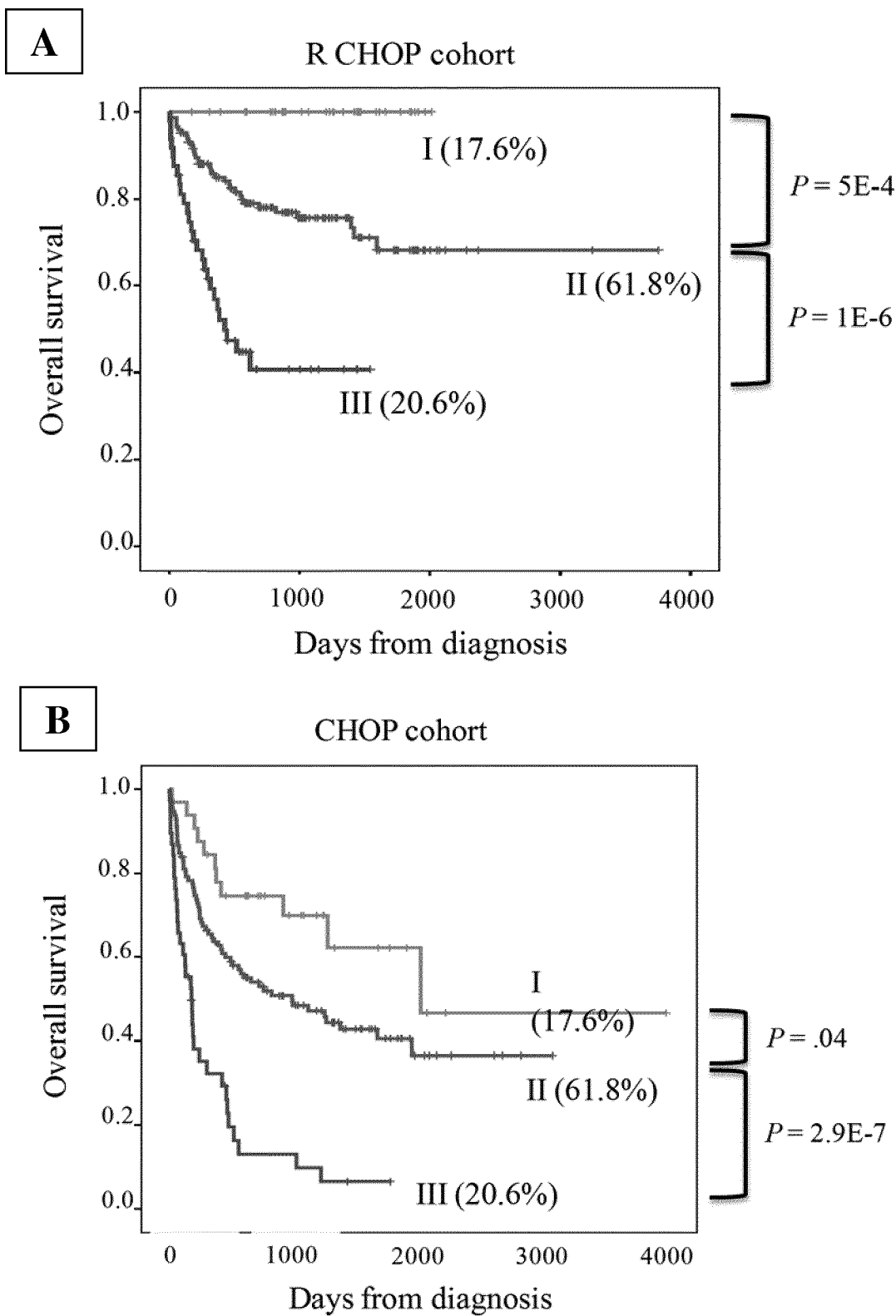

FIG. 4: Combination of the Prognostic Information of FANC, NHEJ and MMR Scores in a DNA Repair Score Patients of the R-CHOP cohort (n=233) were ranked according to increasing DNA repair score and separated in three groups using Maxstat R function (A). The prognostic value of the DNA repair score was validated on an independent cohort of 181 patients treated with CHOP regimen (B).

Figure 5:
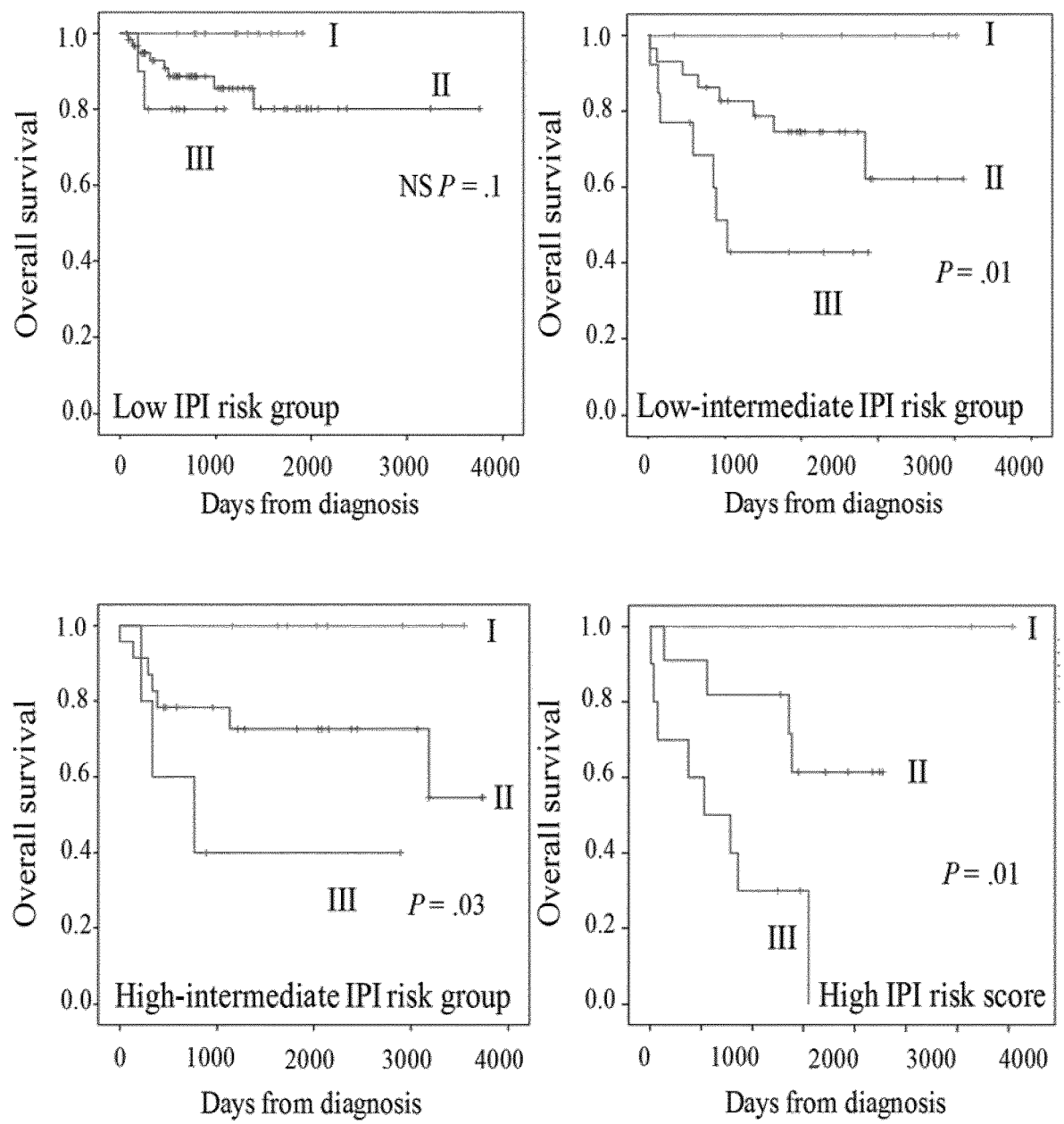

FIG. 5: Prognostic Value of DNA Repair Score for Subgroups of DLBCL Patients Defined by International Prognostic Index (IPI).

DLBCL patients within low, low-intermediate, high-intermediate or high-risk IPI groups were split using DNA repair score. IPI groups: low risk group/IPI score 0 or 1 (n=89), low-intermediate risk group/IPI score 2 (n=49), high-intermediate risk group/IPI score 3 (n=36) and high risk group/IPI score 4 or 5 (n=23).

FIG. 6: FANC (A), NER (B), HRR (C), BER (D), NHEJ (E) and MMR (F) Scores in DLBCL Patients.

Clustergram of genes ordered from best to worst prognosis. The level of the probe set signal is displayed from low to high expression. DLBCL patients (n=233) were ordered by increasing FANC (A), NER (B), HRR (C), BER (D), NHEJ (E) and MMR (F) scores.

FIG. 7: DLBCL Cell Lines Growth Inhibition.

A. DLBCL cell lines growth inhibition by increasing doses of PARP inhibitor (PJ34 hydrochloride). B. The median IC50 was 7.82 µM with a range of 7.19 to 15.15 µM.

EXAMPLES

Example 1

Material & Methods
Patients

Gene expression microarray data from two independent cohorts of patients diagnosed with DLBCL were used. The first cohort comprised 233 patients and was used as a training cohort, and the second one comprised 181 patients and was used as a validation cohort (9). Patients of the training cohort were treated with Rituximab-CHOP regimen and patients of the validation cohort with CHOP regimen. Pre-treatment clinical characteristics of patients were previously published by the group of G. Lenz (9). Affymetrix gene expression data (HG-U133 plus 2.0 microarrays) are publicly available via the online Gene Expression Omnibus (http://www.ncbi.nlm.nih.gov/geo/) under accession number GSE10846. Microarray data were MAS 5 normalized with a scaling factor of 500.

Gene Expression Profiling and Statistical Analyses

The statistical significance of differences in overall survival between groups of patients was calculated by the log-rank test. Multivariate analysis was performed using the Cox proportional hazards model. Survival curves were plotted using the Kaplan-Meier method. All these analyses were done with R version 3.0.2 and Bioconductor version 2.13 (22). Significantly enriched pathways were identified using Reactome functional interaction map (23).

Building the Gene Expression-Based Risk Scores of DNA Repair Pathways.

A consensus list of genes coding for the proteins involved in DNA repair pathways have been obtained using REPAIR-toire database (http://repairtoire.genesilico.pl) (24) and by review of Medline (Tables A, B, C, D, E, F and G). Probe sets were selected for prognostic significance using Maxstat R function and Benjamini Hochberg multiple testing correction. 126 probe sets whose expression value was significantly ($P \le 0.05$) associated with a prognostic value were identified. To gather prognostic information of the Fanconi anemia (FANC), nucleotide excision repair (NER), base excision repair (BER), non-homologous end-joining (NHEJ), mismatch repair (MMR) or homologous recombination repair (HRR) pathway prognostic probe sets within one parameter, FANC, NER, BER, NHEJ, MMR and HRR gene based scores were built as the sum of the beta coefficients weighted by ±1 according to the patient signal above or below the probe set Maxstat value as previously reported (25, 26).

In the validation cohort DNA repair scores were calculated and patients grouped according to the prognostic models and cut-offs from the training cohort. The prognostic value of this scoring was evaluated using log-rank statistics and Cox models.

Gene set enrichment analysis was carried out by computing overlaps with canonical pathways and gene ontology gene sets obtained from the Broad Institute (27).

Results

Identification of DNA Repair Genes Associated with a Prognostic Value in DLBCL Patients A list set of 176 genes involved in six major DNA repair pathways (BER, NER, MMR, HRR, NHEJ and FANC pathways) was defined using the REPAIRtoire database (http://repairtoire.genesilico.pl) (24) and review of the literature (Tables A, B, C, D, E, F and G). Using the Maxstat R function and Benjamini Hochberg multiple testing correction, the inventors found that 126 out of the 176 genes have a prognostic value, including 92 genes with bad and 34 with good prognostic values (Table 1). Poor prognostic genes are displayed using KEGG pathways schemes (http://www.genome.jp/kegg/pathway.html).

A Risk Score Summing Up the Prognostic Information Provided by the Expression of Genes Coding for DNA Repair Pathways in DLBCL For each pathway, a GEP-based risk score was created as the sum of the beta coefficients weighted by ±1 according to the patient signal above or below the probe set Maxstat value as previously reported (26). For each pathways, patients were ranked according to increased prognostic score and for a given score value X, the difference in survival of patients with a prognostic score≤X or >X was computed using Maxstat analysis. High FANC, NER, HRR, BER, NHEJ and MMR scores were significantly associated with a poor prognosis in two cohorts of patients treated with RCHOP or CHOP (FIG. 1A to G). The FANC score includes 30 genes with a bad prognostic value and 3 genes with a good one (Table A, FIG. 6A). The NER score was built with 19 bad prognostic genes and 10 good prognostic genes (Table B, FIG. 6B). The HRR score is based on 40 prognostic genes (33 bad and 7 good) (Table F, FIG. 6C). The BER score was built with 23 genes (18 bad and 5 good) (Table C, FIG. 6D). The NHEJ and MMR scores include respectively 15 (11 bad and 4 good) and 16 (10 bad and 6 good) prognostic genes (Tables D and E and FIGS. 6E and F).

The NER, HRR, BER, NHEJ or MMR scores were significantly higher (P<0.01) in the ABC molecular subgroup compared to the GCB subgroup whereas no significant differences were observed for FANC score (FIG. 2). Interestingly, FANC, NER, HRR, BER, NHEJ and MMR scores have prognostic value in both GCB and ABC molecular subgroups. FANC, NER, HRR, BER, NHEJ and MMR scores segregates patients of the ABC subgroup into a high-risk group with respectively 11.2, 12.6, 12.1, 12.2, 18.6 and 17.8 month median OS and a low risk group with a not reached median OS (P=2.3E-5, P=0.04, P=0.01, P=0.0001, P=0.002 and P=0.003 respectively; FIGS. 3A and B). FANC, NER, HRR, BER, NHEJ and MMR scores separate also patients of the GCB subgroup into a high-risk group and a low risk group (P=0.001, P=0.0001, P=2.8E-7, P=0.001, P=0.006 and P=0.001 respectively; FIGS. 3A and B).

Cox Analysis of DNA Repair Scores Compared with Other Prognostic Factors for OS in DLBCL Patients Cox analysis was used to determine whether the different DNA repair pathway scores provide additional prognostic information compared to previously-identified poor outcome-related factors such as the GERS score, GCB or ABC molecular subgroups and the IPI (low risk group/IPI score 0 or 1, low-intermediate risk group/IPI score 2, high-intermediate risk group/IPI score 3 and high risk group/IPI score 4 or 5). Using univariate analyses, GERS, age, ABC/GCB molecular subgroups, FANC, NER, HRR, BER, NHEJ, MMR scores and IPI had prognostic value (P<0.0001, Table 2A).

Comparing DNA repair scores together, FANC score, NHEJ score and MMR score remained significant (P=0.03, P=0.006 and P=0.02 respectively, Table 2B). When all parameters were tested together, only GERS, FANC score, NHEJ score and MMR score kept prognostic values (Table 2C).

Combining Prognostic Information of FANC Score, NHEJ Score and MMR Score into a Single DNA Repair Based Staging (Combined DNA Repair Score)

Since FANC score, NHEJ score and MMR score displayed independent prognostic information, the inventors combined the prognostic information of the prognostic genes of these three DNA repair scores in a new FANC/NHEJ/MMR combined DNA repair score.

Using Maxstat patients of the RCHOP cohort were classified into three groups according to the combined DNA repair score. Group I was composed of patients with low DNA repair score (n=40), group II comprises patients with intermediate score values (n=144) and group III contains patients with high DNA repair score values (n=48). Group I accounted for 17.6% of patients, group II for 61.8%, group III for 20.6% of patients (FIG. 5A). Patients of groups I and II had a not reached median OS with significant better OS in group I compared to group II (P=5E-4). Group III had the worst prognostic value with a median OS of 13.9 months (FIG. 5A). The prognostic value of the DNA repair score was validated in the CHOP cohort with a significant better survival in the group I (median OS of 132 months) compared to group II (median OS of 64.5 months; P=0.04) and in group 2 compared to group III (11.5 months; P=2.9E-7) (FIG. 5B). Comparing DNA repair score with other poor outcome-related factors such as GERS score, GCB or ABC molecular subgroups and the IPI in multivariate COX analysis, only DNA repair score kept prognostic value (Table 3). The inventors investigated the prognostic value of DNA repair score for subgroups of DLBCL patients defined by IPI. DNA repair score allowed splitting patients in three groups in all IPI subgroups (low risk group/IPI score 0 or 1, low-intermediate risk group/IPI score 2, high-intermediate risk group/IPI score 3 and high risk group/IPI score 4 or 5) (FIG. 5). The prognostic value of the DNA repair score failed to be significant in the low IPI risk group (P=0.1) but segregated DLBCL patients with low-intermediate, high-intermediate and high IPI risk into three significantly different prognostic groups (P=0.01, P=0.03 and P=0.01 respectively) (FIG. 5).

Discussion

The inventors have selected genes coding for proteins involved in DNA repair to build FANC, NER, HRR, BER, NHEJ and MMR scores predictive for overall survival in two cohorts of DLBCL patients. Among these, FANC, BER, NHEJ and MMR scores were shown to be independent predictors for OS when compared to the previously published prognostic factors. When all DNA repair scores were tested together, only FANC, NHEJ and MMR scores remained significant. Interestingly, combining FANC, NHEJ and MMR scores led to a more potent prognostic classification (DNA repair score) of DLBCL patients. Interestingly, the DNA repair score appears to be an excellent prognostic factor in DLBCL patients since only DNA repair score remained a prognostic when compared to age, IPI and ABC or GCB molecular subtypes in multivariate COX analysis (Table 3). B lymphocytes are continuously produced during adult life and they undergo different genetic alterations associated with DNA breaks, including VDJ recombination, Ig class switch recombination (CSR) and somatic hypermutation (SHM) (1, 3). These mechanisms must be tightly regulated to prevent tumorigenesis and ensure efficient immune response (5). Most B cell neoplasms, including DLBCL, emerge form antigen-experienced B cells since IGV genes of malignant cells present somatic hypermutation (SHM) (28). Chromosomal translocations involving the IG loci with breakpoint associated with somatic hypermutation are characteristics of DLBCL (29). DNA repair pathways are deregulated in DLBCL with reported mutations of DNA repair genes including MMR genes (EXO1, MSH2 and MSH6), NHEJ genes (DCLRE11C, PRKDC, XRCC5 and XRCC6), the HR gene BRCA2 and the NER gene DDB1 (12). Furthermore, tumor cells of high-risk patients with DLBCL demonstrated a significant enrichment in genes involved in NER pathway that could represent an adaptive mechanism to drug resistance (20, 21). Several DNA repair inhibitors are currently tested in clinical trials in cancer (19). DLBCL treatments include cyclophosphamide, a nitrogen mustard derivate that induces interstrand crosslinks (ICLs) and doxorubicin, a DNA topoisomerase inhibitor that induce DNA double-strand breaks, DNA adducts and formaldehyde-dependent ICL formation (21). The resistance of cancer cells to DNA damaging drugs involves several mechanisms including drug metabolism, increased DNA repair and anti-apoptotic signaling provided by the tumor environment (30-32). Inhibiting DNA repair is a promising strategy to improve the efficacy of genotoxic drugs and overcome drug resistance (33). Exacerbated toxicity of CHK1 inhibitor was reported in lymphoma cells with upregulated c-Myc expression (34). Myc rearrangements occurs in 5 to 10% of DLBCL patients and is associated with a worse prognostic in patient cohorts treated with CHOP (35, 36) and RCHOP regimens (37, 38). Myc can also be activated and overexpressed by amplification, mutations, micro RNA-dependent mechanisms or by epigenetic mechanisms (39-42). These data support the view that inhibitors of DNA damage signaling and DNA repair have potential therapeutic interest in DLBCL. A number of DNA damage response inhibitors have been developed, including inhibitors of ATM, ATR, PARP, CHK1, CHK2, WEE1, CDC25, APE1, DNA-PKs, RAD51 and MGMT, and some of them are tested in clinical trials (19, 33, 34).

Despite overall improvements in the treatment of DLBCL, including the use of rituximab, approximately one third of patients fail to achieve complete remission or they experience relapse. This remains a major cause of morbidity and mortality. The current DNA repair scores could be useful to identify high-risk DLBCL patients and exploit addiction to a specific DNA repair pathway in order to define the best DNA repair inhibitor to employ in combination with conventional treatment. Furthermore, these DNA repair scores could be useful at different times of treatment and especially at relapse to define targeted therapies that have greater effectiveness and render resistant tumors responsive to treatment. Recent data provide evidence that DLBCL relapse may result from multiple different evolutionary mechanisms (44). According to this clonal heterogeneity, the DNA repair scores could be valuable to identify the adapted targeted treatment corresponding to drug resistance mechanisms selected during clonal evolution. These advances may limit the side effects of treatment, improving compliance with dosing regimens and overall quality of life.

TABLE 1

Identification of DNA repair genes whose expression is associated with a prognostic value in DLBCL patients.

| Probeset | Name | Maxstat cutPoint | Benjamini Hochberg corrected p value | Hazard ratio | Pathways |
| --- | --- | --- | --- | --- | --- |
| 210027_s_at | APEX1 | 6822 | 2.54E-02 | 1.480 | BER |
| 204408_at | APEX2 | 422 | 4.11E-03 | 2.045 | BER |
| 241379_at | APLF | 149 | 2.60E-03 | 0.528 | NHEJ |
| 218527_at | APTX | 1166 | 5.52E-05 | 2.076 | BER |
| 208442_s_at | ATM | 357 | 4.63E-03 | 1.648 | Fanconi/HRR/NHEJ |
| 1552937_s_at | ATRIP | 759 | 4.45E-04 | 2.146 | Fanconi |
| 205345_at | BARD1 | 1903 | 3.34E-02 | 0.506 | HRR |
| 204531_s_at | BRCA1 | 656 | 4.49E-03 | 1.968 | Fanconi/HRR |
| 214727_at | BRCA2 | 324 | 1.68E-02 | 1.666 | Fanconi/HRR |
| 221800_s_at | C17orf70 | 578 | 2.69E-04 | 1.871 | Fanconi |
| 214816_x_at | C19orf40 | 220 | 1.03E-02 | 1.618 | Fanconi/HRR |
| 204093_at | CCNH | 2674 | 4.05E-03 | 0.623 | NER |
| 209194_at | CETN2 | 1055 | 4.07E-03 | 0.561 | NER |
| 205394_at | CHEK1 | 1541 | 1.01E-02 | 1.696 | Fanconi |
| 210416_s_at | CHEK2 | 624 | 3.52E-03 | 1.638 | HRR |
| 203229_s_at | CLK2 | 2246 | 2.20E-04 | 1.961 | Fanconi |
| 202467_s_at | COPS2 | 5039 | 7.15E-03 | 0.632 | NER |
| 202078_at | COPS3 | 1963 | 1.68E-02 | 1.519 | NER |
| 218042_at | COPS4 | 2910 | 4.66E-03 | 0.633 | NER |
| 201652_at | COPS5 | 3816 | 3.41E-04 | 0.537 | NER |
| 209029_at | COPS7A | 1461 | 9.61E-05 | 2.029 | NER |
| 219997_s_at | COPS7B | 593 | 2.10E-03 | 1.966 | NER |
| 236204_at | COPS8 | 89 | 1.35E-02 | 0.676 | NER |
| 201423_s_at | CUL4A | 1480 | 2.13E-04 | 1.919 | NER |
| 208619_at | DDB1 | 4243 | 4.68E-03 | 1.624 | NER |
| 208386_x_at | DMC1 | 94 | 3.26E-02 | 0.712 | HRR |
| 234464_s_at | EME1 | 687 | 1.28E-02 | 1.619 | Fanconi/HRR |

TABLE 1-continued

Identification of DNA repair genes whose expression is
associated with a prognostic value in DLBCL patients.

| Probeset | Name | Maxstat cutPoint | Benjamini Hochberg corrected p value | Hazard ratio | Pathways |
|---|---|---|---|---|---|
| 1569868_s_at | EME2 | 372 | 3.73E−03 | 1.640 | HRR |
| 213579_s_at | EP300 | 612 | 5.38E−04 | 0.547 | NER |
| 213468_at | ERCC2 | 240 | 1.39E−04 | 1.965 | NER |
| 202176_at | ERCC3 | 671 | 1.34E−02 | 1.515 | NER |
| 235215_at | ERCC4 | 617 | 3.14E−03 | 1.858 | Fanconi/NER |
| 202414_at | ERCC5 | 1414 | 2.50E−03 | 0.477 | NER |
| 205162_at | ERCC8 | 397 | 3.64E−04 | 1.865 | NER |
| 204603_at | EXO1 | 735 | 1.57E−04 | 1.938 | HRR/MMR |
| 203678_at | FAN1 | 400 | 3.82E−03 | 1.808 | Fanconi |
| 203805_s_at | FANCA | 1250 | 8.30E−04 | 1.770 | Fanconi |
| 1557217_a_at | FANCB | 24 | 1.40E−03 | 0.570 | Fanconi |
| 205189_s_at | FANCC | 473 | 1.24E−03 | 1.749 | Fanconi |
| 223545_at | FANCD2 | 322 | 1.01E−03 | 1.811 | Fanconi |
| 220255_at | FANCE | 198 | 6.18E−03 | 2.701 | Fanconi |
| 222713_s_at | FANCF | 669 | 8.01E−03 | 1.677 | Fanconi |
| 203564_at | FANCG | 1429 | 1.46E−05 | 2.286 | Fanconi |
| 213008_at | FANCI | 509 | 3.33E−02 | 1.977 | Fanconi |
| 224683_at | FBXO18 | 910 | 2.76E−04 | 1.933 | HRR |
| 228286_at | GEN1 | 2174 | 2.19E−02 | 1.644 | HRR |
| 202451_at | GTF2H1 | 1520 | 8.19E−03 | 0.631 | NER |
| 203577_at | GTF2H4 | 407 | 8.88E−04 | 1.883 | NER |
| 213357_at | GTF2H5 | 2494 | 4.33E−03 | 0.624 | NER |
| 200943_at | HMGN1 | 19838 | 2.52E−03 | 0.560 | NER |
| 204883_s_at | HUS1 | 762 | 2.48E−03 | 0.575 | BER |
| 225357_s_at | INO80 | 461 | 5.66E−06 | 2.838 | HRR |
| 65133_i_at | INO80B | 271 | 2.83E−04 | 1.855 | HRR |
| 1559716_at | INO80C | 221 | 1.48E−04 | 2.035 | HRR |
| 227931_at | INO80D | 746 | 1.31E−03 | 0.483 | HRR |
| 227286_at | INO80E | 1030 | 1.49E−04 | 1.959 | HRR |
| 214258_x_at | KAT5 | 1098 | 3.75E−04 | 1.849 | HRR |
| 202726_at | LIG1 | 1038 | 3.66E−04 | 1.867 | BER/MMR/NER |
| 207348_s_at | LIG3 | 229 | 1.70E−05 | 2.184 | BER/NER |
| 206235_at | LIG4 | 174 | 4.78E−04 | 0.525 | NHEJ |
| 202520_s_at | MLH1 | 3167 | 1.34E−02 | 1.599 | Fanconi/MMR |
| 202167_s_at | MMS19 | 1523 | 1.48E−02 | 2.056 | NER |
| 203565_s_at | MNAT1 | 616 | 1.35E−02 | 0.649 | NER |
| 205395_s_at | MRE11A | 784 | 1.98E−03 | 0.585 | HRR |
| 205887_x_at | MSH3 | 594 | 3.64E−03 | 0.565 | MMR |
| 210533_at | MSH4 | 89 | 1.32E−02 | 1.590 | HRR |
| 210410_s_at | MSH5 | 413 | 4.77E−03 | 1.596 | HRR |
| 202911_at | MSH6 | 3593 | 3.71E−04 | 0.545 | MMR |
| 218463_s_at | MUS81 | 1353 | 4.45E−03 | 1.615 | Fanconi/HRR |
| 207727_s_at | MUTYH | 1404 | 4.83E−05 | 2.076 | BER |
| 202907_s_at | NBN | 3272 | 6.80E−04 | 1.799 | HRR |
| 219396_s_at | NEIL1 | 353 | 4.60E−03 | 0.629 | BER |
| 226585_at | NEIL2 | 300 | 2.73E−04 | 1.899 | BER |
| 219502_at | NEIL3 | 288 | 4.97E−03 | 1.655 | BER |
| 219418_at | NHEJ1 | 354 | 7.16E−04 | 1.946 | NHEJ |
| 210470_x_at | NONO | 2755 | 3.50E−03 | 1.720 | NHEJ |
| 209731_at | NTHL1 | 560 | 2.01E−04 | 2.176 | BER |
| 205301_s_at | OGG1 | 266 | 1.82E−02 | 0.587 | BER |
| 215773_x_at | PARP2 | 1925 | 2.52E−03 | 1.918 | BER |
| 209940_at | PARP3 | 510 | 1.33E−04 | 1.975 | NHEJ |
| 201202_at | PCNA | 9365 | 1.20E−02 | 0.663 | BER/MMR/NER |
| 221206_at | PMS2 | 985 | 1.22E−03 | 1.718 | Fanconi/MMR |
| 218961_s_at | PNKP | 958 | 4.22E−05 | 2.069 | BER |
| 203422_at | POLD1 | 1732 | 1.94E−05 | 2.553 | HRR/BER/MMR/NER |
| 201115_at | POLD2 | 1006 | 2.84E−04 | 2.108 | HRR/BER/MMR/NER |
| 202996_at | POLD4 | 1701 | 9.56E−03 | 0.660 | HRR/BER/MMR/NER |
| 216026_s_at | POLE | 486 | 4.94E−03 | 1.678 | BER/MMR/NER |
| 233852_at | POLH | 642 | 8.51E−03 | 1.538 | Fanconi/BER |
| 219317_at | POLI | 424 | 1.46E−02 | 1.490 | Fanconi |
| 221049_s_at | POLL | 58 | 3.28E−02 | 1.600 | BER/NHEJ |
| 222238_s_at | POLM | 791 | 2.89E−04 | 2.190 | NHEJ |
| 242804_at | POLN | 24 | 1.28E−02 | 2.446 | Fanconi |
| 210543_s_at | PRKDC | 983 | 2.80E−04 | 1.877 | NHEJ |
| 201046_s_at | RAD23A | 4507 | 8.48E−04 | 1.833 | NER |
| 201222_at | RAD23B | 5821 | 7.77E−03 | 1.634 | NER |
| 208393_s_at | RAD50 | 1298 | 2.01E−02 | 1.440 | HRR |
| 205024_s_at | RAD51 | 1352 | 7.85E−03 | 1.558 | Fanconi/HRR |
| 37793_r_at | RAD51D | 307 | 4.99E−05 | 2.230 | HRR |
| 205647_at | RAD52 | 187 | 1.33E−03 | 1.765 | HRR |
| 218117_at | RBX1 | 5431 | 4.04E−03 | 0.593 | NER |

TABLE 1-continued

Identification of DNA repair genes whose expression is
associated with a prognostic value in DLBCL patients.

| Probeset | Name | Maxstat cutPoint | Benjamini Hochberg corrected p value | Hazard ratio | Pathways |
|---|---|---|---|---|---|
| 218428_s_at | REV1 | 1095 | 6.85E−03 | 1.628 | Fanconi |
| 1053_at | RFC2 | 591 | 2.04E−03 | 0.550 | MMR |
| 204127_at | RFC3 | 1677 | 7.18E−03 | 1.901 | MMR |
| 204023_at | RFC4 | 2753 | 2.00E−02 | 1.721 | MMR |
| 201529_s_at | RPA1 | 3026 | 1.36E−03 | 1.705 | Fanconi/HRR/MMR/NER |
| 201756_at | RPA2 | 3573 | 1.32E−03 | 1.758 | Fanconi/HRR/NER |
| 209507_at | RPA3 | 5753 | 1.70E−03 | 0.583 | Fanconi/HRR/MMR/NER |
| 206092_x_at | RTEL1 | 251 | 1.35E−04 | 2.005 | HRR |
| 206554_x_at | SETMAR | 495 | 4.51E−03 | 1.837 | NHEJ |
| 201585_s_at | SFPQ | 1935 | 4.63E−03 | 1.584 | NHEJ |
| 218317_x_at | SLX1 | 859 | 2.67E−04 | 2.304 | Fanconi |
| 212275_s_at | SRCAP | 366 | 2.19E−04 | 2.153 | HRR |
| 214299_at | TOP3A | 338 | 1.20E−04 | 1.988 | Fanconi/HRR |
| 202330_s_at | UNG | 2120 | 6.60E−03 | 1.595 | BER |
| 202412_s_at | USP1 | 1146 | 2.59E−04 | 0.516 | Fanconi |
| 233893_s_at | UVSSA | 662 | 3.77E−04 | 1.897 | NER |
| 65591_at | WDR48 | 990 | 1.36E−04 | 2.142 | Fanconi |
| 218110_at | XAB2 | 339 | 7.12E−04 | 1.764 | NER |
| 205672_at | XPA | 774 | 6.49E−03 | 1.715 | NER |
| 209375_at | XPC | 1073 | 8.01E−03 | 0.624 | NER |
| 203655_at | XRCC1 | 576 | 7.82E−03 | 1.548 | BER/NER |
| 207598_x_at | XRCC2 | 492 | 4.46E−03 | 0.372 | HRR |
| 216299_s_at | XRCC3 | 342 | 1.88E−04 | 2.034 | HRR |
| 205072_s_at | XRCC4 | 265 | 2.13E−02 | 0.697 | NHEJ |
| 232633_at | XRCC5 | 142 | 9.85E−03 | 0.662 | NHEJ |
| 200792_at | XRCC6 | 11903 | 3.10E−02 | 1.405 | NHEJ |

TABLE 2

Cox univariate and multivariate analysis of OS in
DLBCL patient's R-CHOP cohort (n = 233)

A.

| Prognostic variable | Overall survival (n = 233) | |
|---|---|---|
| | HR | p value |
| GERS | 4.62 | <.0001 |
| Age (>60 years) | 2.2 | <.0001 |
| GCB-ABC molecular subgroups | 2.75 | <.0001 |
| IPI | 1.79 | <.0001 |
| FANC | 3.87 | <.0001 |
| NER | 3.64 | <.0001 |
| HRR | 4.37 | <.0001 |
| BER | 4.19 | <.0001 |
| NHEJ | 7.30 | <.0001 |
| MMR | 4.09 | <.0001 |

B.

| | Overall survival (n = 233) | |
|---|---|---|
| FANC | 2.01 | .03 |
| NER | 1.01 | NS |
| HRR | 1.27 | NS |
| BER | 1.78 | NS |
| NHEJ | 4.29 | .006 |
| MMR | 2.17 | .02 |

C.

| Prognostic variable | Overall survival (n = 233) | |
|---|---|---|
| | HR | p value |
| GERS | 3.49 | .001 |
| Age (>60 years) | 2.09 | NS |
| GCB-ABC molecular subgroups | 1.96 | NS |
| IPI | 1.22 | NS |
| FANC | 2.29 | .04 |
| NER | 0.80 | NS |
| HRR | 1.43 | NS |
| BER | 2.20 | NS |
| NHEJ | 7.05 | .009 |
| MMR | 3.49 | .003 |

The prognostic factors were tested as single variable (A) or multivariables (B, C) using Cox-model. P-values and the hazard ratios (HR) are shown. NS: not significant at a 5% threshold.

TABLE 3

Cox univariate and multivariate analysis of OS in DLBCL patient's R-CHOP cohort (n = 233) including DNA repair score.

| Prognostic variable | Overall survival (n = 233) | |
| --- | --- | --- |
| | HR | p value |
| A. | | |
| GERS | 4.62 | <.0001 |
| Age (>60 years) | 2.2 | <.0001 |
| GCB-ABC molecular subgroups | 2.75 | <.0001 |
| IPI | 1.79 | <.0001 |
| DNA repair score | 3.8 | <.0001 |
| B. | | |
| GERS | 1.99 | NS |
| Age (>60 years) | 0.93 | NS |
| GCB-ABC molecular subgroups | 1.72 | NS |
| IPI | 1.19 | NS |
| DNA repair score | 2.26 | .008 |

The prognostic factors were tested as single variable (A) or multivariables (B) using Cox-model. P-values and the hazard ratios (HR) are shown. NS: not significant at a 5% threshold.

Example 2

All the 18 DLBCL cell lines (OCILY4, SUDHL6, SUDHL4, HT, SUDHL2, OCILY1, OCILY10, OCILY3, OCILY8, OCILY19, SUDHL10, DOHH2, U2932, OCILY18, OCILY7, SUDHL8, KARPAS231 and WSU NHL) investigated have FANC, NER, BER, MMR, HRR, NHEJ and DNA repair scores superior to the cutoff defined for each score. Accordingly, DLBCL cell lines are sensitive to DNA Damage Response (DDR) inhibition using CHK inhibitors (at submicromolar concentrations) as previously reported (67).

The pharmacological inhibitors of poly(ADP-ribose) polymerase-1 (PARP-1) have been included in the arsenal of anti-cancer drugs by showing consistent benefits in clinical trials against BRCA-mutant cancers that are deficient in the homologous recombination repair (HRR) of DNA double strand breaks (DSB). PARP-1 is a multifunctional protein implicated in various cellular responses to DNA damage ranging from different pathways of DNA repair and cell death to stress signaling, transcription, and genomic stability.

The effects of PARPi were initially linked to inhibition of PARP-1 functions in base excision repair (BER) of DNA damaged by replication stress or genotoxic agents, resulting in accumulation of single strand breaks, which upon conversion to toxic DSB lesions would kill cancer cells deficient in DSB DNA repair.

Figure 7A:
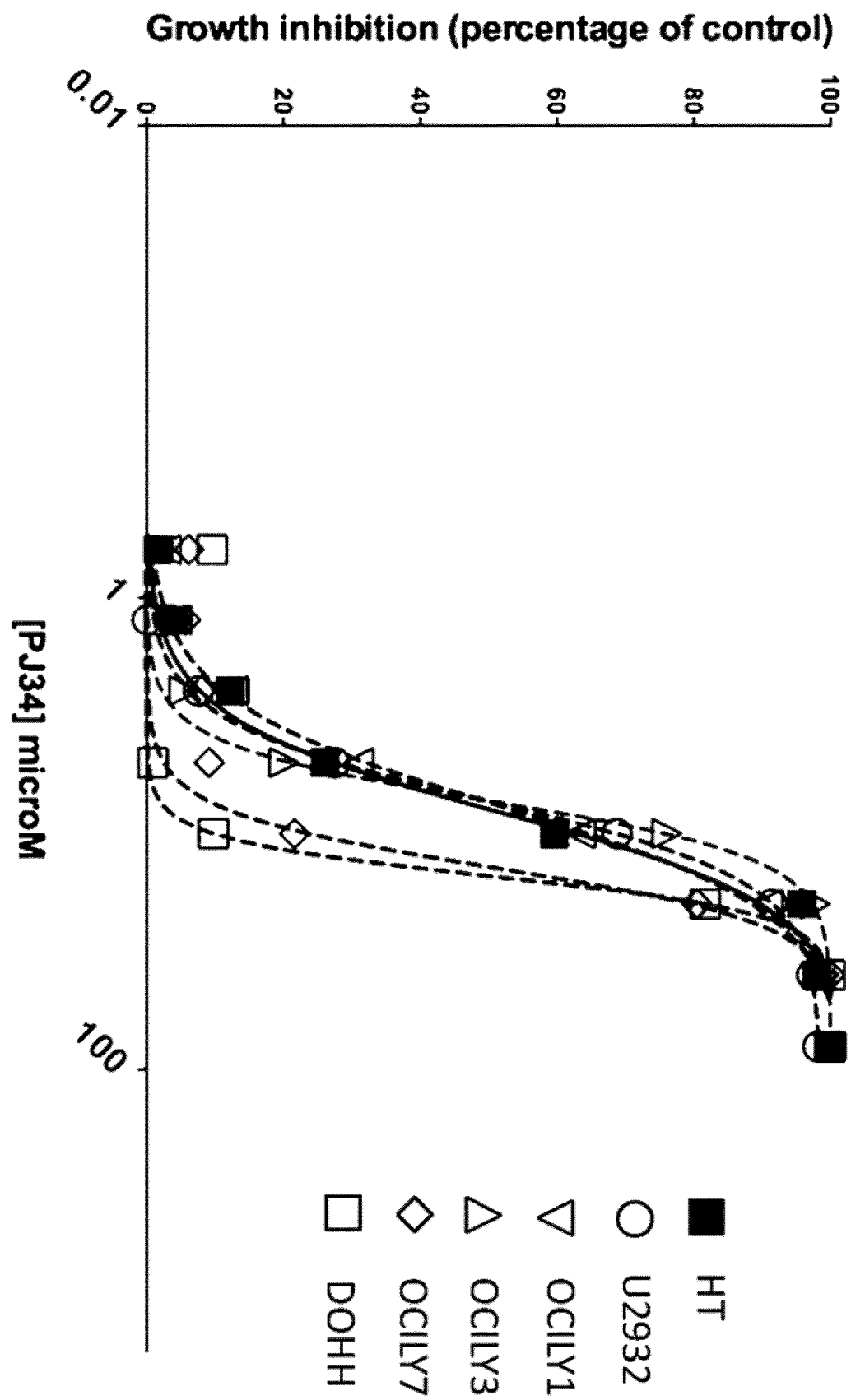
Figure 7B:
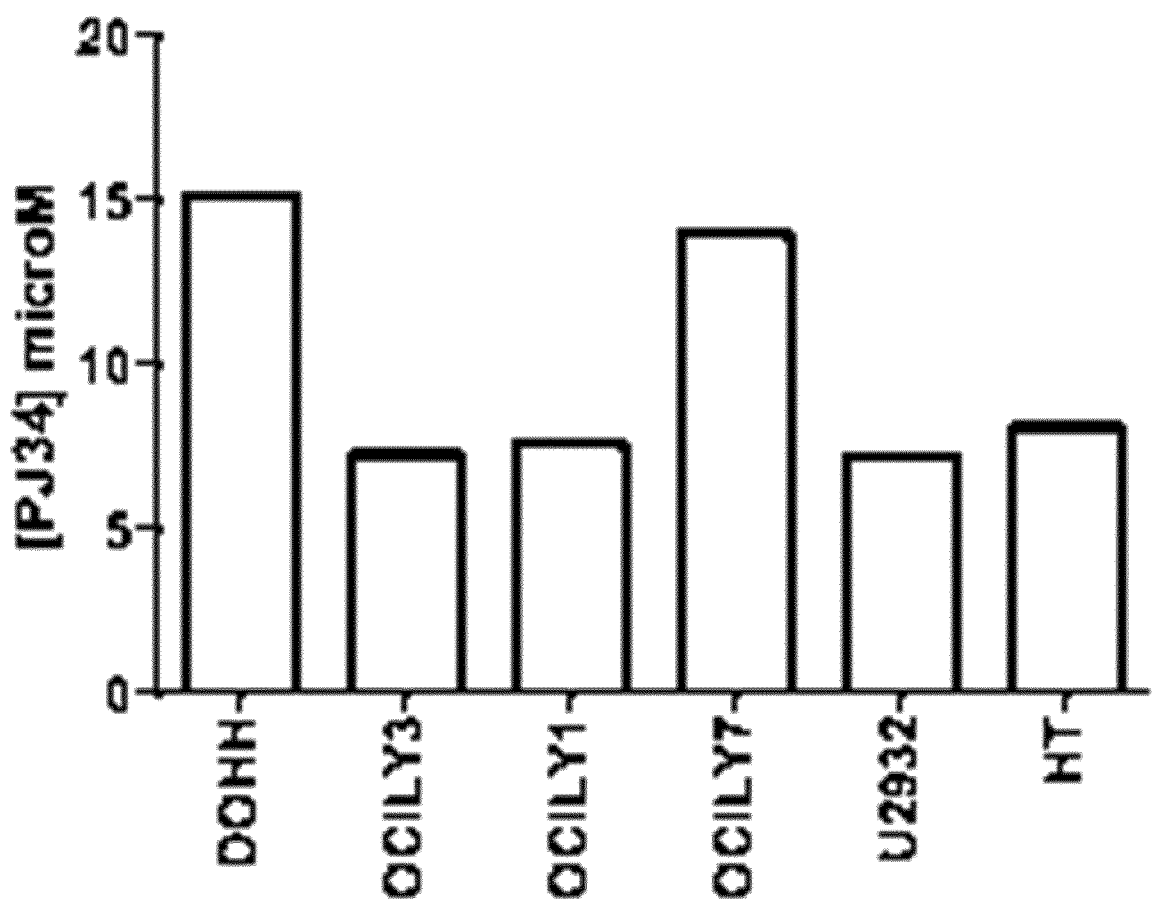

6 DLBCL cell lines were treated by increasing doses of PARP inhibitor (PJ34 hydrochloride). DLBCL cell lines growth was quantified with a Cell Titer Glo Luminescent Assay (Promega, Madison, Wis., USA) and the 50% inhibitory concentration (IC50) was determined using GraphPad Prism software (http://www.graphpad.com/scientific-software/prism/) (FIG. 7A). The median IC50 was 7.82 µM with a range of 7.19 to 15.15 µM (FIG. 7B).

Interestingly, the HRR score could predict for DLBCL cell sensitivity to PARPi. The two DLBCL cell lines with high HRR score exhibited a 2-fold higher resistance to PARPi (IC50: 15.15 and 13.95 µM for DOHH and OCILY7 respectively) compared to DLBCL cell lines with a lower HRR score (median IC50=7.41 µM; range: 7.19 to 8.08 µM) (Table 4).

According to the role of PARP1 in BER (68), DLBCL cell lines with a high BER score were sensitive to PARPi excluding the cell lines with a high HRR score.

The BER and HRR scores could be valuable for adapting targeted PARPi treatment in DLBCL patients with high BER/low HRR score values and improve the efficacy of genotoxic drugs used in DLBCL therapy.

None of the other MMR, NHEJ, FANC and DNA repair scores could predict the sensitivity of DLBCL cells to PARPi.

TABLE 4

DLBCL cell lines HRR score.

| | HRR score | PJ34 IC50 microM |
| --- | --- | --- |
| HT | −4.233012064 | 8.084 |
| OCILY3 | −1.308528364 | 7.258 |
| OCILY4 | −1.222708248 | |
| OCILY1 | −1.090661456 | 7.572 |
| SUDHL10 | −0.7223597 | |
| U2932 | −0.507499675 | 7.199 |
| OCILY8 | −0.32904285 | |
| SUDHL2 | 0.683461654 | |
| OCILY19 | 0.693030696 | |
| OCILY18 | 1.821968683 | |
| OCILY10 | 2.895780098 | |
| Daudi | 3.099955497 | |
| SUDHL4 | 3.92262264 | |
| DOHH2 | 3.973755482 | 15.15 |
| OCILY7 | 6.945403653 | 13.95 |
| SUDHL8 | 8.049216902 | |

REFERENCES

Throughout this application, various references describe the state of the art to which this invention pertains. The disclosures of these references are hereby incorporated by reference into the present disclosure.

1. Jung D, Giallourakis C, Mostoslaysky R, Alt F W. Mechanism and control of V(D)J recombination at the immunoglobulin heavy chain locus. Annu Rev Immunol 2006; 24: 541-70.
2. Kotnis A, Du L, Liu C, Popov S W, Pan-Hammarstrom Q. Non-homologous end joining in class switch recombination: the beginning of the end. Philosophical transactions of the Royal Society of London Series B, Biological sciences 2009; 364: 653-65.
3. Di Noia J M, Neuberger M S. Molecular mechanisms of antibody somatic hypermutation. Annual review of biochemistry 2007; 76: 1-22.
4. Stavnezer J, Bjorkman A, Du L, Cagigi A, Pan-Hammarstrom Q. Mapping of switch recombination junctions, a tool for studying DNA repair pathways during immunoglobulin class switching. Adv Immunol 2010; 108: 45-109.
5. Chiarle R. Translocations in normal B cells and cancers: insights from new technical approaches. Adv Immunol 2013; 117: 39-71.
6. Siegel R, Naishadham D, Jemal A. Cancer statistics, 2012. CA: a cancer journal for clinicians 2012; 62: 10-29.
7. Staudt L M, Dave S. The biology of human lymphoid malignancies revealed by gene expression profiling. Adv Immunol 2005; 87: 163-208.

8. Lenz G, Staudt L M. Aggressive lymphomas. N Engl J Med 2010; 362: 1417-29.
9. Lenz G, Wright G, Dave S S, Xiao W, Powell J, Zhao H, Xu W, Tan B, Goldschmidt N, Iqbal J, Vose J, Bast M, et al. Stromal gene signatures in large-B-cell lymphomas. N Engl J Med 2008; 359: 2313-23.
10. Rosenwald A, Wright G, Chan W C, Connors J M, Campo E, Fisher R I, Gascoyne R D, Muller-Hermelink H K, Smeland E B, Giltnane J M, Hurt E M, Zhao H, et al. The use of molecular profiling to predict survival after chemotherapy for diffuse large-B-cell lymphoma. N Engl J Med 2002; 346: 1937-47.
11. Wright G, Tan B, Rosenwald A, Hurt E H, Wiestner A, Staudt L M. A gene expression-based method to diagnose clinically distinct subgroups of diffuse large B cell lymphoma. Proc Natl Acad Sci USA 2003; 100: 9991-6.
12. de Miranda N F, Peng R, Georgiou K, Wu C, Falk Sorqvist E, Berglund M, Chen L, Gao Z, Lagerstedt K, Lisboa S, Roos F, van Wezel T, et al. DNA repair genes are selectively mutated in diffuse large B cell lymphomas. J Exp Med 2013; 210: 1729-42.
13. Luo J, Solimini N L, Elledge S J. Principles of cancer therapy: oncogene and non-oncogene addiction. Cell 2009; 136: 823-37.
14. Kennedy R D, D'Andrea A D. DNA repair pathways in clinical practice: lessons from pediatric cancer susceptibility syndromes. J Clin Oncol 2006; 24: 3799-808.
15. Savitsky K, Bar-Shira A, Gilad S, Rotman G, Ziv Y, Vanagaite L, Tagle D A, Smith S, Uziel T, Sfez S, Ashkenazi M, Pecker I, et al. A single ataxia telangiectasia gene with a product similar to PI-3 kinase. Science 1995; 268: 1749-53.
16. McKinnon P J, Caldecott K W. DNA strand break repair and human genetic disease. Annual review of genomics and human genetics 2007; 8: 37-55.
17. Futreal P A, Liu Q, Shattuck-Eidens D, Cochran C, Harshman K, Tavtigian S, Bennett L M, Haugen-Strano A, Swensen J, Miki Y, et al. BRCA1 mutations in primary breast and ovarian carcinomas. Science 1994; 266: 120-2.
18. Wooster R, Bignell G, Lancaster J, Swift S, Seal S, Mangion J, Collins N, Gregory S, Gumbs C, Micklem G. Identification of the breast cancer susceptibility gene BRCA2. Nature 1995; 378: 789-92.
19. Shaheen M, Allen C, Nickoloff J A, Hromas R. Synthetic lethality: exploiting the addiction of cancer to DNA repair. Blood 2011; 117: 6074-82.
20. Bret C, Klein B, Moreaux J. Gene expression-based risk score in diffuse large B-cell lymphoma. Oncotarget 2012; 3: 1700-10.
21. Bret C, Klein B, Moreaux J. Nucleotide excision DNA repair pathway as a therapeutic target in patients with high-risk diffuse large B cell lymphoma. Cell Cycle 2013; 12: 1811-2.
22. Gentleman R C, Carey V J, Bates D M, Bolstad B, Dettling M, Dudoit S, Ellis B, Gautier L, Ge Y, Gentry J, Hornik K, Hothorn T, et al. Bioconductor: open software development for computational biology and bioinformatics. Genome Biol 2004; 5: R80.
23. Vastrik I, D'Eustachio P, Schmidt E, Gopinath G, Croft D, de Bono B, Gillespie M, Jassal B, Lewis S, Matthews L, Wu G, Birney E, et al. Reactome: a knowledge base of biologic pathways and processes. Genome Biol 2007; 8: R39.
24. Milanowska K, Krwawicz J, Papaj G, Kosinski J, Poleszak K, Lesiak J, Osinska E, Rother K, Bujnicki J M. REPAIRtoire—a database of DNA repair pathways. Nucleic Acids Res 2011; 39: D788-92.
25. Bou Samra E, Klein B, Commes T, Moreaux J. Development of gene expression-based risk score in cytogenetically normal acute myeloid leukemia patients. Oncotarget 2012; 3: 824-32.
26. Kassambara A, Hose D, Moreaux J, Walker B A, Protopopov A, Reme T, Pellestor F, Pantesco V, Jauch A, Morgan G, Goldschmidt H, Klein B. Genes with a spike expression are clustered in chromosome (sub)bands and spike (sub)bands have a powerful prognostic value in patients with multiple myeloma. Haematologica 2012; 97: 622-30.
27. Subramanian A, Tamayo P, Mootha V K, Mukherjee S, Ebert B L, Gillette M A, Paulovich A, Pomeroy S L, Golub T R, Lander E S, Mesirov J P. Gene set enrichment analysis: a knowledge-based approach for interpreting genome-wide expression profiles. Proc Natl Acad Sci USA 2005; 102: 15545-50.
28. Klein U, Dalla-Favera R. Germinal centres: role in B-cell physiology and malignancy. Nat Rev Immunol 2008; 8: 22-33.
29. Lenz G, Nagel I, Siebert R, Roschke A V, Sanger W, Wright G W, Dave S S, Tan B, Zhao H, Rosenwald A, Muller-Hermelink H K, Gascoyne R D, et al. Aberrant immunoglobulin class switch recombination and switch translocations in activated B cell-like diffuse large B cell lymphoma. J Exp Med 2007; 204: 633-43.
30. Chen C C, Taniguchi T, D'Andrea A. The Fanconi anemia (FA) pathway confers glioma resistance to DNA alkylating agents. J Mol Med (Berl) 2007; 85: 497-509.
31. Taniguchi T, Tischkowitz M, Ameziane N, Hodgson S V, Mathew C G, Joenje H, Mok S C, D'Andrea A D. Disruption of the Fanconi anemia-BRCA pathway in cisplatin-sensitive ovarian tumors. Nat Med 2003; 9: 568-74.
32. Helleday T. Homologous recombination in cancer development, treatment and development of drug resistance. Carcinogenesis 2010; 31: 955-60.
33. Curtin N J. Inhibiting the DNA damage response as a therapeutic manoeuvre in cancer. British journal of pharmacology 2013; 169: 1745-65.
34. Ferrao P T, Bukczynska E P, Johnstone R W, McArthur G A. Efficacy of CHK inhibitors as single agents in MYC-driven lymphoma cells. Oncogene 2012; 31: 1661-72.
35. Yoon S O, Jeon Y K, Paik J H, Kim W Y, Kim Y A, Kim J E, Kim C W. MYC translocation and an increased copy number predict poor prognosis in adult diffuse large B-cell lymphoma (DLBCL), especially in germinal centre-like B cell (GCB) type. Histopathology 2008; 53: 205-17.
36. Klapper W, Stoecklein H, Zeynalova S, Ott G, Kosari F, Rosenwald A, Loeffler M, Trumper L, Pfreundschuh M, Siebert R, German High-Grade Non-Hodgkin's Lymphoma Study G. Structural aberrations affecting the MYC locus indicate a poor prognosis independent of clinical risk factors in diffuse large B-cell lymphomas treated within randomized trials of the German High-Grade Non-Hodgkin's Lymphoma Study Group (DSHNHL). Leukemia 2008; 22: 2226-9.
37. Barrans S, Crouch S, Smith A, Turner K, Owen R, Patmore R, Roman E, Jack A. Rearrangement of MYC is associated with poor prognosis in patients with diffuse large B-cell lymphoma treated in the era of rituximab. J Clin Oncol 2010; 28: 3360-5.
38. Savage K J, Johnson N A, Ben-Neriah S, Connors J M, Sehn L H, Farinha P, Horsman D E, Gascoyne R D. MYC gene rearrangements are associated with a poor prognosis 39. Leucci E, Cocco M, Onnis A, De Falco G, van Cleef P, Bellan C, van Rijk A, Nyagol J, Byakika B, Lazzi S, Tosi P, van Krieken H, et al. MYC translocation-negative classical Burkitt lymphoma cases: an alternative pathogenetic mechanism involving miRNA deregulation. J Pathol 2008; 216: 440-50.

40. Onnis A, De Falco G, Antonicelli G, Onorati M, Bellan C, Sherman O, Sayed S, Leoncini L. Alteration of microRNAs regulated by c-Myc in Burkitt lymphoma. PLoS One 2010; 5.

41. Stasik C J, Nitta H, Zhang W, Mosher C H, Cook J R, Tubbs R R, Unger J M, Brooks T A, Persky D O, Wilkinson S T, Grogan T M, Rimsza L M. Increased MYC gene copy number correlates with increased mRNA levels in diffuse large B-cell lymphoma. Haematologica 2010; 95: 597-603.

42. Chapuy B, McKeown M R, Lin C Y, Monti S, Roemer M G, Qi J, Rahl P B, Sun H H, Yeda K T, Doench J G, Reichert E, Kung A L, et al. Discovery and characterization of super-enhancer-associated dependencies in diffuse large B cell lymphoma. Cancer Cell 2013; 24: 777-90.

43. Curtin N J. DNA repair dysregulation from cancer driver to therapeutic target. Nat Rev Cancer 2012; 12: 801-17.

44. Redmond D, Nie K, Eng K, Clozel T, Martin P, Tan L, Melnick A M, Tam W, Elemento O. Deep Sequencing Reveals Clonal Evolution Patterns and Mutation Events Associated With Relapse In B Cell Lymphomas. Blood 2013; 122: 79.

45. Hickson, I., et al., Identification and characterization of a novel and specific inhibitor of the ataxia-telangiectasia mutated kinase ATM. Cancer Res, 2004. 64(24): p. 9152-9.

46. Li, Y. and D. Q. Yang, The ATM inhibitor KU-55933 suppresses cell proliferation and induces apoptosis by blocking Akt in cancer cells with overactivated Akt. Mol Cancer Ther, 2010. 9(1): p. 113-25.

47. Golding, S. E., et al., Improved ATM kinase inhibitor KU-60019 radiosensitizes glioma cells, compromises insulin, AKT and ERK prosurvival signaling, and inhibits migration and invasion. Mol Cancer Ther, 2009. 8(10): p. 2894-902.

48. Peasland, A., et al., Identification and evaluation of a potent novel ATR inhibitor, NU6027, in breast and ovarian cancer cell lines. Br J Cancer, 2011. 105(3): p. 372-81.

49. Reaper, P. M., et al., Selective killing of ATM- or p53-deficient cancer cells through inhibition of ATR. Nat Chem Biol, 2011. 7(7): p. 428-30.

50. Prevo, R., et al., The novel ATR inhibitor VE-821 increases sensitivity of pancreatic cancer cells to radiation and chemotherapy. Cancer Biol Ther, 2012. 13(11): p. 1072-81.

51. Charrier, J. D., et al., Discovery of potent and selective inhibitors of ataxia telangiectasia mutated and Rad3 related (ATR) protein kinase as potential anticancer agents. J Med Chem, 2011. 54(7): p. 2320-30.

52. Toledo, L. I., et al., A cell-based screen identifies ATR inhibitors with synthetic lethal properties for cancer-associated mutations. Nat Struct Mol Biol, 2011. 18(6): p. 721-7.

53. Leahy, J. J., et al., Identification of a highly potent and selective DNA-dependent protein kinase (DNA-PK) inhibitor (NU7441) by screening of chromenone libraries. Bioorg Med Chem Lett, 2004. 14(24): p. 6083-7.

54. Zhao, Y., et al., Preclinical evaluation of a potent novel DNA-dependent protein kinase inhibitor NU7441. Cancer Res, 2006. 66(10): p. 5354-62.

55. Veuger, S. J., et al., Radiosensitization and DNA repair inhibition by the combined use of novel inhibitors of DNA-dependent protein kinase and poly(ADP-ribose) polymerase-1. Cancer Res, 2003. 63(18): p. 6008-15.

56. Willmore, E., et al., A novel DNA-dependent protein kinase inhibitor, NU7026, potentiates the cytotoxicity of topoisomerase II poisons used in the treatment of leukemia. Blood, 2004. 103(12): p. 4659-65.

57. Munck, J. M., et al., Chemosensitization of cancer cells by KU-0060648, a dual inhibitor of DNA-PK and PI-3K. Mol Cancer Ther, 2012. 11(8): p. 1789-98.

58. Rainey, M. D., et al., Transient inhibition of ATM kinase is sufficient to enhance cellular sensitivity to ionizing radiation. Cancer Res, 2008. 68(18): p. 7466-74.

59. Tang, Y., et al., Poly(ADP-ribose) polymerase 1 modulates the lethality of CHK1 inhibitors in mammary tumors. Mol Pharmacol, 2012. 82(2): p. 322-32.

60. Brezak, M. C., et al., IRC-083864, a novel bis quinone inhibitor of CDC25 phosphatases active against human cancer cells. Int J Cancer, 2009. 124(6): p. 1449-56.

61. Ying, S., F. C. Hamdy, and T. Helleday, Mre11-dependent degradation of stalled DNA replication forks is prevented by BRCA2 and PARP1. Cancer Res, 2012. 72(11): p. 2814-21.

62. Neher, T. M., et al., Novel irreversible small molecule inhibitors of replication protein A display single-agent activity and synergize with cisplatin. Mol Cancer Ther, 2011. 10(10): p. 1796-806.

63. Huang, F., et al., Inhibition of homologous recombination in human cells by targeting RAD51 recombinase. J Med Chem, 2012. 55(7): p. 3011-20.

64. Budke, B., et al., RI-1: a chemical inhibitor of RAD51 that disrupts homologous recombination in human cells. Nucleic Acids Res, 2012. 40(15): p. 7347-57.

65. Shaheen, M., et al., Synthetic lethality: exploiting the addiction of cancer to DNA repair. Blood, 2011. 117(23): p. 6074-82.

66. Sabharwal, A., et al., A phase I trial of lomeguatrib and irinotecan in metastatic colorectal cancer. Cancer Chemother Pharmacol, 2010. 66(5): p. 829-35.

67. Derenzini E, Agostinelli C, Imbrogno E, et al. Constitutive activation of the DNA damage response pathway as a novel therapeutic target in diffuse large B-cell lymphoma. Oncotarget. Mar. 30, 2015; 6(9):6553-6569.

68. Shah G M, Robu M, Purohit N K, Rajawat J, Tentori L, Graziani G. PARP Inhibitors in Cancer Therapy: Magic Bullets but Moving Targets. Frontiers in oncology. 2013; 3:279.

The invention claimed is:

1. A method for the treatment of diffuse large B-cell lymphoma in a patient in need thereof and able to respond to a DNA repair pathway inhibitor comprising the steps of:
   a) identifying the patient able to respond to a DNA repair pathway inhibitor by
      i) determining an expression level (ELi) for each gene of a gene set selected from the group consisting in the gene set of table A, wherein said genes are FANCE, POLN, SLX1, FANCG, WDR48, ATRIP, TOP3A, FANCI, CLK2, C17orf70/FAAP100, ERCC4, FANCD2, FANI, FANCA, RPA2, FANCC, PMS2, RPAI, CHEK1, FANCF, BRCA2, ATM, REVI, EMEI, C19orf40/FAAP24, MUS81, MLH1, RAD51, POLH, POL1, RPA3, FANCB and USP1, the gene set of table B, wherein said genes are POLD1, LIG3, MMS19, ERCC2, CUL4A, UVSSA, GTF2H4/TFIIH4, LIG1, ERCC8, ERCC4, RAD23A, XAB2, RPA2, XPA, RPA1, POLE, RAD23B, DDB1, ERCC3, PCNA, MNAT1, GTF2H1/TFIIH1, GTF2H5/TFIIH5, XPC, CCNH, RBX1, RPA3, CETN2 and ERCC5, the gene set of table C, wherein said genes are POLD1, LIG3, NTHL1, POLD2, APTX, MUTYH, PNKP, APEX2, PARP2, NEIL2, LIG1, POLE, NEIL3, POLL, UNG, XRCC1, POLH, APEX1, PCNA, POLD4, NEIL1, OGG1 and HUS1, the gene set of table D, wherein said genes are POLM, PNKP, PARP3, NHEJ1, PRKDC, SETMAR, NONO, ATM, POLL, SFPQ, XRCC6, XRCC4, XRCC5, APLF and LIG4, the gene set of table E, wherein said genes are POLD1, POLD2, EXO1, RFC3, LIG1, RFC4, PMS2, RPA1, POLE, MLH1, PCNA, POLD4, RPA3, MSH3, RFC2 and MSH6, the gene set of table F, wherein said genes are INO80, POLD1, RAD51D, SRCAP, POLD2, INO80C, XRCC3, RTEL1, TOP3A, BRCA1, INO80E, EXO1, FBX018, INO80B, KATS, NBN, RAD52, RPA2, RPA1, BRCA2, ATM, GEN1, EME2, CHEK2, EME1, C19orf40, MUS81, MSH5, MSH4, MCM9, RAD51, RAD51B, RAD50, DMC1, POLD4, MRE11A, RPA3, BARD1, INO80D and XRCC2, the gene set of table G, wherein said genes are FANCE, POLD1, POLN, SLX1, FANCG, POLM, ATRIP, WDR48, POLD2, PNKP, TOP3A, FANC1, PARP3, CLK2, NHEJ1, EXO1, RFC3, PRKDC, C17orf70/FAAP100, LIG1, ERCC4, SETMAR, FANCD2, FAN1, FANCA, RPA2, FANCC, RFC4, NONO, PMS2, RPA1, CHEK1, POLE, FANCF, BRCA2, ATM, REV1, EME1, C19orf40/FAAP24, MUS81, POLL, MLH1, SFPQ, RAD51, POLH, POL1, XRCC6, XRCC4, PCNA, XRCC5, POLD4, RPA3, FANCB, MSH3, RFC2, MSH6, APLF, LIG4 and USP1, and a combination thereof, in a biological sample obtained from said patient, ii) comparing each expression level (ELi) determined at step i) with a predetermined reference level (ELRi), iii) calculating the DNARS score trough the following formula $$DNARS = \sum_{i=1}^{n} \beta i \times Ci$$

wherein βi represent the regression β coefficient reference value for the gene $G_i$ and Ci=1 if the expression of the gene Gi (ELi) is higher than the predetermined reference level (ELRi) or Ci=−1 if the expression of the gene (ELi) is lower than or equal to the predetermined reference level (ELRi), iv) comparing the score DNARS determined at step iii) with a predetermined reference value $DNARS_R$, and v) confirming that the DNARS score is higher than the predetermined reference value $DNARS_R$, and concluding that the patient able to respond to the DNA repair pathway inhibitor, and b) administering the DNA repair pathway inhibitor to the patient.

2. The method for the treatment of diffuse large B-cell lymphoma in a patient in need thereof according to claim 1, wherein step a) is identifying the patient able to respond to a Fanconi DNA repair pathway inhibitor,
wherein the gene set in step i) is of table A,
wherein the DNARS score is a FANC DNARS score,
wherein the reference value $DNARS_R$ is a reference value FANC $DNARS_R$, and wherein step b) is the administration of the Fanconi DNA repair pathway inhibitor.

3. The method for the treatment of diffuse large B-cell lymphoma in a patient in need thereof according to claim 1, wherein step a) is identifying the patient able to respond to a nucleotide excision DNA repair pathway inhibitor,
wherein the gene set in step i) is of table B,
wherein the DNARS score is a NER DNARS score,
wherein the reference value $DNARS_R$ is a reference value NER $DNARS_R$, and wherein step b) is the administration of the nucleotide excision DNA repair pathway inhibitor.

4. The method for the treatment of diffuse large B-cell lymphoma in a patient in need thereof according to claim 1, wherein step a) is identifying the patient able to respond to a base excision DNA repair pathway inhibitor,
wherein the gene set in step i) is of table C,
wherein the DNARS score is a BER DNARS score,
wherein the reference value $DNARS_R$ is a reference value BER $DNARS_R$, and wherein step b) is the administration of the base excision DNA repair pathway inhibitor.

5. The method for the treatment of diffuse large B-cell lymphoma in a patient in need thereof according to claim 1, wherein step a) is identifying the patient able to respond to a non-homologous end-joining DNA repair pathway inhibitor,
wherein the gene set in step i) is of table D,
wherein the DNARS score is a NHEJ DNARS score,
wherein the reference value $DNARS_R$ is a reference value NHEJ $DNARS_R$, and wherein step b) is the administration of the non-homologous end-joining DNA repair pathway inhibitor.

6. The method for the treatment of diffuse large B-cell lymphoma in a patient in need thereof according to claim 1, wherein step a) is identifying the patient able to respond to a mismatch DNA repair pathway inhibitor,
wherein the gene set in step i) is of table E,
wherein the DNARS score is a MMR DNARS score,
wherein the reference value $DNARS_R$ is a reference value MMR $DNARS_R$, and wherein step b) is the administration of the mismatch DNA repair pathway inhibitor.

7. The method for the treatment of diffuse large B-cell lymphoma in a patient in need thereof according to claim 1, wherein step a) is identifying the patient able to respond to a homologous recombination DNA repair pathway inhibitor,
wherein the gene set in step i) is of table F,
wherein the DNARS score is a HRR DNARS score,
wherein the reference value $DNARS_R$ is a reference value HRR $DNARS_R$, and wherein step b) is the administration of the homologous recombination DNA repair pathway inhibitor.

8. The method for the treatment of diffuse large B-cell lymphoma in a patient in need thereof according to claim 1, wherein step a) is identifying the patient able to respond to a DNA repair pathway inhibitor targeting several DNA repair pathways,
wherein the gene set in step i) is of table G, and
wherein step b) is the administration of the DNA repair pathway inhibitor targeting several DNA repair pathways.

9. The method for the treatment of diffuse large B-cell lymphoma in a patient in need thereof according to claim 1, wherein step a) is identifying the patient able to respond to at least 2 DNA repair pathway inhibitors selected in the group consisting in Fanconi DNA repair pathway inhibitor, non-homologous end-joining DNA repair pathway inhibitor, and mismatch DNA repair pathway inhibitor,
  wherein the gene set in step i) is of table G, and
  wherein step b) is the administration of the at least 2 DNA repair pathway inhibitors selected in the group consisting in Fanconi DNA repair pathway inhibitor, non-homologous end-joining DNA repair pathway inhibitor, and mismatch DNA repair pathway inhibitor.

10. A method for the treatment of diffuse large B-cell lymphoma in a patient in need thereof and able to respond to a PARP inhibitor comprising the steps of:
  a) identifying the patient able to respond to a PARP inhibitor by
    i) determining an expression level (ELi) for each gene of the gene set of table C, wherein said genes are POLD1, LIG3, NTHL1, POLD2, APTX, MUTYH, PNKP, APEX2, PARP2, NEIL2, LIG1, POLE, NEIL3, POLL, UNG, XRCC1, POLH, APEX1, PCNA, POLD4, NEIL1, OGG1 and HUS1, and
    determining an expression level (ELi) for each gene of the gene set of table F, wherein said genes are INO80, POLD1, RAD51D, SRCAP, POLD2, INO80C, XRCC3, RTEL1, TOP3A, BRCA1, INO80E, EXO1, FBXO18, INO80B, KATS, NBN, RAD52, RPA2, RPA1, BRCA2, ATM, GEN1, EME2, CHEK2, EME1, C19orf40, MUS81, MSH5, MSH4, MCM9, RAD51, RAD51B, RAD50, DMC1, POLD4, MRE11A, RPA3, BARD1, INO80D and XRCC2,
    in a biological sample obtained from said patient,
    ii) comparing each expression level (ELi) determined at step i) for the gene set of table C with a predetermined reference level (ELRi), and comparing each expression level (ELi) determined at step i) for the gene set of table F with a predetermined reference level (ELRi),
    iii) calculating a BER DNARS score for the gene set of table C, and a HRR DNARS score for the gene set of table F,
    wherein the first DNARS and the second DNARS are each calculating trough the following formula $$DNARS = \sum_{i=1}^{n} \beta i \times Ci$$

wherein βi represent the regression β coefficient reference value for the gene $G_i$ and Ci=1 if the expression of the gene Gi (ELi) is higher than the predetermined reference level (ELRi) or Ci=−1 if the expression of the gene (ELi) is lower than or equal to the predetermined reference level (ELRi),
    iv) comparing the score BER DNARS determined at step iii) with a predetermined reference value BER $DNARS_R$, and comparing the score HRR DNARS determined at step iii) with a predetermined reference value HRR $DNARS_R$, and
    vi) confirming that the BER DNARS score is higher than the predetermined reference value BER $DNARS_R$, confirming that the HRR DNARS score is lower than the predetermined reference value HRR $DNARS_R$, and concluding that the patient is able to respond to the PARP inhibitor, and
  b) administering the PARP inhibitor to the patient.

* * * * *